(12) United States Patent
Tan et al.

(10) Patent No.: US 10,018,566 B2
(45) Date of Patent: Jul. 10, 2018

(54) PARTIALLY ENCAPSULATED WAVEGUIDE BASED SENSING CHIPS, SYSTEMS AND METHODS OF USE

(71) Applicant: LDIP, LLC, Thousand Oaks, CA (US)

(72) Inventors: Ming Tan, Danville, CA (US); Yun-Pei Chang, Arcadia, CA (US); Leyla Sabet, Los Angeles, CA (US); Ashutosh Shastry, Santa Clara, CA (US); Christopher E. Todd, Campbell, CA (US); Reuven Duer, Thousand Oaks, CA (US)

(73) Assignee: LDIP, LLC, Thousand Oaks, CA (US)

( * ) Notice: Subject to any disclaimer, the term of this patent is extended or adjusted under 35 U.S.C. 154(b) by 164 days.

(21) Appl. No.: 14/813,015

(22) Filed: Jul. 29, 2015

(65) Prior Publication Data

US 2016/0033412 A1    Feb. 4, 2016

Related U.S. Application Data

(60) Provisional application No. 62/030,473, filed on Jul. 29, 2014.

(51) Int. Cl.
| | |
|---|---|
| *C12M 1/34* | (2006.01) |
| *G01N 21/77* | (2006.01) |
| *G01N 33/543* | (2006.01) |
| *B01L 3/00* | (2006.01) |
| *G01N 21/64* | (2006.01) |

(52) U.S. Cl.
CPC .......... *G01N 21/7703* (2013.01); *B01L 3/502* (2013.01); *G01N 33/54373* (2013.01);
(Continued)

(58) Field of Classification Search
CPC ................................................. G01N 33/54373
(Continued)

(56) References Cited

U.S. PATENT DOCUMENTS

| | | |
|---|---|---|
| 4,394,060 A | 7/1983 | Verber et al. |
| 4,444,879 A | 4/1984 | Foster et al. |

(Continued)

FOREIGN PATENT DOCUMENTS

| | | |
|---|---|---|
| EP | 598213 B1 | 7/1997 |
| EP | 737308 B1 | 3/1998 |

(Continued)

OTHER PUBLICATIONS andrew.cmu.edu; Evanescent Waves; printed from http://andrew.cmu.edu/user/dcprieve/Evanescent%20waves.htm on Aug. 22, 2012; 2 pages.

(Continued)

*Primary Examiner* — Chris L Chin
(74) *Attorney, Agent, or Firm* — Shay Glenn LLP

(57) ABSTRACT

Optical readers and alignment tools for detecting the level of an analyte. Described herein are small, disposable partially-encapsulated sensing chips for detecting an analyte level from a fluid sample (e.g., a blood sample) having an edge of the integrated sensing chip exposed to directly expose a plurality of excitation and a collection waveguides, as well as optical readers and methods of operating them. A fluid sample maybe applied to a sensing surface of the sensing chip in the housing so that an analyte level can be optically detected. Also described are methods of sensing an analyte using these devices and systems including an optical detector.

21 Claims, 8 Drawing Sheets

(52) U.S. Cl.
CPC . *B01L 2200/025* (2013.01); *B01L 2200/0605* (2013.01); *B01L 2200/0684* (2013.01); *B01L 2200/16* (2013.01); *B01L 2300/0663* (2013.01); *B01L 2300/0681* (2013.01); *B01L 2400/0406* (2013.01); *B01L 2400/049* (2013.01); *B01L 2400/0487* (2013.01); *B01L 2400/06* (2013.01); *G01N 21/648* (2013.01)

(58) Field of Classification Search
USPC .................................................. 422/82.11
See application file for complete search history.

(56) References Cited

U.S. PATENT DOCUMENTS

| | | |
|---|---|---|
| 4,478,485 A | 10/1984 | Khoe et al. |
| 4,515,430 A | 5/1985 | Johnson |
| 4,651,343 A | 3/1987 | Laor |
| 4,744,623 A | 5/1988 | Prucnal et al. |
| 4,746,179 A | 5/1988 | Dahne et al. |
| 4,799,797 A | 1/1989 | Huggins |
| 4,815,843 A | 3/1989 | Tiefenthaler et al. |
| 4,820,016 A | 4/1989 | Cohen et al. |
| 4,838,631 A | 6/1989 | Chande et al. |
| 4,850,666 A | 7/1989 | Izutsu et al. |
| RE33,064 E | 9/1989 | Carter et al. |
| 4,876,446 A | 10/1989 | Kambe et al. |
| 4,881,789 A | 11/1989 | Levinson |
| 4,889,407 A | 12/1989 | Markle et al. |
| 4,906,837 A | 3/1990 | Doneen et al. |
| 4,940,328 A | 7/1990 | Hartman |
| 4,978,503 A | 12/1990 | Shanks et al. |
| 4,998,792 A | 3/1991 | Boerstler et al. |
| 5,031,987 A | 7/1991 | Norling |
| 5,075,494 A | 12/1991 | Gassen |
| 5,077,878 A | 1/1992 | Armiento et al. |
| 5,081,012 A | 1/1992 | Flanagan et al. |
| 5,120,131 A | 6/1992 | Lukosz |
| 5,121,457 A | 6/1992 | Foley et al. |
| 5,151,480 A | 9/1992 | Podszun et al. |
| 5,173,747 A | 12/1992 | Boiarski et al. |
| 5,208,111 A | 5/1993 | Decher et al. |
| 5,217,568 A | 6/1993 | Tessier et al. |
| 5,340,715 A | 8/1994 | Slovacek et al. |
| 5,344,784 A | 9/1994 | Attridge |
| 5,377,008 A | 12/1994 | Ridgway et al. |
| 5,439,647 A | 8/1995 | Saini |
| 5,440,388 A | 8/1995 | Erickson |
| 5,444,805 A | 8/1995 | Mayer |
| 5,455,178 A | 10/1995 | Fattinger |
| 5,479,260 A | 12/1995 | Fattinger |
| 5,494,798 A | 2/1996 | Gerdt et al. |
| 5,496,701 A | 3/1996 | Pollard-Knight |
| 5,512,492 A | 4/1996 | Herron et al. |
| 5,547,839 A | 8/1996 | Dower et al. |
| 5,573,956 A | 11/1996 | Hanning |
| 5,577,137 A | 11/1996 | Groger et al. |
| 5,581,646 A | 12/1996 | Tsukamoto et al. |
| 5,585,639 A | 12/1996 | Dorsel et al. |
| 5,600,744 A | 2/1997 | Takahashi |
| 5,614,386 A | 3/1997 | Metzker et al. |
| 5,621,031 A | 4/1997 | Leimann et al. |
| 5,623,561 A | 4/1997 | Hartman |
| 5,631,170 A | 5/1997 | Attridge |
| 5,635,608 A | 6/1997 | Haugland et al. |
| 5,640,234 A | 6/1997 | Roth et al. |
| 5,671,303 A | 9/1997 | Shieh et al. |
| 5,677,196 A | 10/1997 | Herron et al. |
| 5,677,769 A | 10/1997 | Bendett |
| 5,710,000 A | 1/1998 | Sapolsky et al. |
| 5,712,937 A | 1/1998 | Asawa et al. |
| 5,728,529 A | 3/1998 | Metzker et al. |
| 5,734,768 A | 3/1998 | Kim et al. |
| 5,737,457 A | 4/1998 | Saini et al. |
| 5,800,992 A | 9/1998 | Fodor et al. |
| 5,814,565 A | 9/1998 | Reichert et al. |
| 5,822,472 A | 10/1998 | Danielzik et al. |
| 5,830,766 A | 11/1998 | Attridge et al. |
| 5,832,165 A | 11/1998 | Reichert et al. |
| 5,861,242 A | 1/1999 | Chee et al. |
| 5,872,243 A | 2/1999 | Gee et al. |
| 5,919,712 A | 7/1999 | Herron et al. |
| 5,998,796 A | 12/1999 | Liu et al. |
| 6,027,880 A | 2/2000 | Cronin et al. |
| 6,040,403 A | 3/2000 | Starzewski |
| 6,057,466 A | 5/2000 | Starzewski et al. |
| 6,078,705 A | 6/2000 | Neuschafer et al. |
| 6,108,463 A | 8/2000 | Herron et al. |
| 6,110,749 A | 8/2000 | Obremski et al. |
| 6,137,117 A | 10/2000 | Feldstein et al. |
| 6,141,465 A | 10/2000 | Bischel et al. |
| 6,191,852 B1 | 2/2001 | Paffhaen et al. |
| 6,222,619 B1 | 4/2001 | Herron et al. |
| 6,228,575 B1 | 5/2001 | Gingeras et al. |
| 6,239,876 B1 | 5/2001 | Brandenberg |
| 6,242,267 B1 | 6/2001 | Herron et al. |
| 6,287,871 B1 | 9/2001 | Herron et al. |
| 6,316,274 B1 | 11/2001 | Herron et al. |
| 6,335,793 B1 | 1/2002 | Freeman et al. |
| 6,361,947 B1 | 3/2002 | Dong et al. |
| 6,384,912 B2 | 5/2002 | Kra et al. |
| 6,389,186 B1 | 5/2002 | DiGiovanni et al. |
| 6,395,558 B1 | 5/2002 | Duveneck et al. |
| 6,396,995 B1 | 5/2002 | Stuelpnagel et al. |
| 6,437,345 B1 | 8/2002 | Bruno-Raimondi et al. |
| 6,465,241 B2 | 10/2002 | Haronian et al. |
| 6,469,785 B1 | 10/2002 | Duveneck et al. |
| 6,483,096 B1 | 11/2002 | Kunz et al. |
| 6,492,468 B1 | 12/2002 | Chen et al. |
| 6,498,041 B1 | 12/2002 | Tabacco et al. |
| 6,522,408 B1 | 2/2003 | Bruck et al. |
| 6,580,941 B2 | 6/2003 | Webb |
| 6,618,536 B1 | 9/2003 | Heideman et al. |
| 6,632,609 B2 | 10/2003 | Lizardi |
| 6,661,938 B2 | 12/2003 | Lim et al. |
| 6,713,264 B2 | 3/2004 | Luttermann et al. |
| 6,759,663 B2 | 7/2004 | Tsipouras |
| 6,767,733 B1 | 7/2004 | Green |
| 6,777,244 B2 | 8/2004 | Pepper et al. |
| 6,785,432 B2 | 8/2004 | Letant et al. |
| 6,801,677 B1 | 10/2004 | Grace et al. |
| 6,830,936 B2 | 12/2004 | Anderson et al. |
| 6,847,746 B2 | 1/2005 | Uchiyama |
| 6,870,165 B2 | 3/2005 | Amirkhanian et al. |
| 6,947,634 B2 | 9/2005 | Tanaka et al. |
| 6,951,715 B2 | 10/2005 | Cunningham et al. |
| 6,956,651 B2 | 10/2005 | Lackritz et al. |
| 6,961,490 B2 | 11/2005 | Maisenhoelder et al. |
| 6,974,673 B2 | 12/2005 | Lockhart |
| 6,987,898 B2 | 1/2006 | Tran |
| 7,046,893 B2 | 5/2006 | Dorn et al. |
| 7,057,031 B2 | 6/2006 | Olejnik et al. |
| 7,058,255 B1 | 6/2006 | Fang |
| 7,101,945 B2 | 9/2006 | Dorn et al. |
| 7,122,012 B2 | 10/2006 | Bouton et al. |
| 7,175,811 B2 | 2/2007 | Bach et al. |
| 7,203,386 B2 | 4/2007 | Krol et al. |
| 7,227,147 B2 | 6/2007 | Riehle et al. |
| RE39,772 E | 8/2007 | Herron et al. |
| 7,292,336 B2 | 11/2007 | Cunningham et al. |
| 7,308,166 B1 | 12/2007 | Peng et al. |
| 7,313,424 B2 | 12/2007 | Mayevsky et al. |
| 7,349,080 B2 | 3/2008 | Aklian |
| 7,358,079 B2 | 4/2008 | Schürmann-Mader et al. |
| 7,373,063 B2 | 5/2008 | Nakata et al. |
| 7,396,675 B2 | 7/2008 | Pawlak et al. |
| 7,410,784 B2 | 8/2008 | Hatch |
| 7,444,053 B2 | 10/2008 | Schmidt et al. |
| 7,447,391 B2 | 11/2008 | Peled et al. |
| 7,483,140 B1 | 1/2009 | Cho et al. |
| 7,545,494 B2 | 6/2009 | Haiml et al. |
| 7,627,201 B2 | 12/2009 | Tiefenthaler |
| 7,708,945 B1 | 5/2010 | Abel et al. |
| 7,764,374 B2 | 7/2010 | Hubner et al. |
| 7,768,650 B2 | 8/2010 | Bazlenko |

(56) References Cited

U.S. PATENT DOCUMENTS

| | | |
|---|---|---|
| 7,811,754 B2 | 10/2010 | Herron et al. |
| 7,820,983 B2 | 10/2010 | Lundquist et al. |
| 7,838,847 B2 | 11/2010 | Lundquist et al. |
| 7,879,598 B2 | 2/2011 | Zesch et al. |
| 7,922,976 B2 | 4/2011 | Dutta et al. |
| 7,951,583 B2 | 5/2011 | Duer |
| 8,187,866 B2 | 5/2012 | Duer |
| 8,238,993 B2 | 8/2012 | Maynard et al. |
| 8,288,157 B2 | 10/2012 | Duer |
| 8,675,199 B2 | 3/2014 | Duer |
| 8,747,751 B2 | 6/2014 | Duer et al. |
| 9,423,397 B2 | 8/2016 | Duer |
| 2001/0055462 A1 | 12/2001 | Seibel |
| 2002/0045811 A1 | 4/2002 | Kittrell et al. |
| 2002/0114576 A1 | 8/2002 | Schroeder |
| 2002/0126936 A1 | 9/2002 | Lockhart |
| 2002/0126938 A1 | 9/2002 | Lockhart |
| 2002/0168780 A1 | 11/2002 | Liu et al. |
| 2002/0172457 A1 | 11/2002 | Tapalian et al. |
| 2002/0197456 A1 | 12/2002 | Pope |
| 2003/0063851 A1 | 4/2003 | Hillendahl et al. |
| 2003/0091277 A1 | 5/2003 | Mei |
| 2003/0108274 A1 | 6/2003 | Haronian |
| 2003/0108291 A1 | 6/2003 | Duveneck et al. |
| 2003/0138208 A1 | 7/2003 | Pawlak et al. |
| 2003/0169956 A1 | 9/2003 | Lange et al. |
| 2004/0008919 A1 | 1/2004 | Freeman et al. |
| 2004/0020987 A1 | 2/2004 | Nishioka et al. |
| 2004/0022475 A1 | 2/2004 | Pennington |
| 2004/0023396 A1 | 2/2004 | Boyd et al. |
| 2004/0036949 A1 | 2/2004 | Trezza |
| 2004/0046128 A1 | 3/2004 | Abel et al. |
| 2004/0052489 A1 | 3/2004 | Duveneck et al. |
| 2004/0081384 A1 | 4/2004 | Datesman et al. |
| 2004/0105644 A1 | 6/2004 | Dawes |
| 2004/0142370 A1 | 7/2004 | Dosmann et al. |
| 2004/0191119 A1 | 9/2004 | Zanzucchi et al. |
| 2004/0197044 A1 | 10/2004 | Bloom |
| 2005/0018949 A1 | 1/2005 | Yan |
| 2005/0043139 A1 | 2/2005 | Kennedy |
| 2005/0088648 A1 | 4/2005 | Grace et al. |
| 2005/0089261 A1 | 4/2005 | Shimazaki |
| 2005/0110989 A1 | 5/2005 | Schermer |
| 2005/0145783 A1 | 7/2005 | Zheng |
| 2005/0153320 A1 | 7/2005 | Herron et al. |
| 2005/0163659 A1 | 7/2005 | Duveneck et al. |
| 2005/0175273 A1 | 8/2005 | Lida et al. |
| 2005/0195394 A1 | 9/2005 | Ma et al. |
| 2005/0196102 A1 | 9/2005 | Yamazaki et al. |
| 2005/0201657 A1 | 9/2005 | Tiefenthaler |
| 2005/0201659 A1 | 9/2005 | Strecker |
| 2005/0227231 A1 | 10/2005 | Tcherkassov |
| 2005/0254744 A1 | 11/2005 | Freeman |
| 2006/0008227 A1 | 1/2006 | Schmidt et al. |
| 2006/0014151 A1 | 1/2006 | Ogura et al. |
| 2006/0061754 A1 | 3/2006 | Turner et al. |
| 2006/0072873 A1 | 4/2006 | Tekippe et al. |
| 2006/0073491 A1 | 4/2006 | Joseph et al. |
| 2006/0078889 A1 | 4/2006 | Bhattacharjee et al. |
| 2006/0098927 A1 | 5/2006 | Schmidt et al. |
| 2006/0115230 A1 | 6/2006 | Komoguchi et al. |
| 2006/0183145 A1 | 8/2006 | Turner |
| 2007/0077595 A1 | 4/2007 | Koo et al. |
| 2007/0222704 A1 | 9/2007 | Huang |
| 2007/0231458 A1 | 10/2007 | Gale et al. |
| 2007/0231880 A1 | 10/2007 | Chang-Yen et al. |
| 2008/0117418 A1 | 5/2008 | Claps et al. |
| 2008/0243181 A1 | 10/2008 | Schneider et al. |
| 2009/0069199 A1 | 3/2009 | Brandenburg |
| 2009/0142790 A1 | 6/2009 | Fang et al. |
| 2010/0072396 A1 | 3/2010 | Agranat et al. |
| 2010/0167413 A1 | 7/2010 | Lundquist et al. |
| 2010/0202925 A1 | 8/2010 | Sonnleitner |
| 2010/0248352 A1 | 9/2010 | Song et al. |
| 2010/0256016 A1 | 10/2010 | Blair et al. |
| 2010/0279429 A1 | 11/2010 | Hildenbrand et al. |
| 2011/0028346 A1 | 2/2011 | Chakravarty et al. |
| 2012/0196383 A1 | 8/2012 | Nitkowski et al. |
| 2012/0231532 A1 | 9/2012 | Duer |
| 2013/0063726 A1 | 3/2013 | Monro et al. |
| 2013/0071850 A1 | 3/2013 | Duer |
| 2014/0180271 A1 | 6/2014 | Duer |
| 2017/0023477 A1 | 1/2017 | Duer et al. |
| 2017/0067829 A1 | 3/2017 | Duer |
| 2017/0082617 A1 | 3/2017 | Duer |
| 2018/0031476 A1 | 2/2018 | Duer |

FOREIGN PATENT DOCUMENTS

| | | |
|---|---|---|
| EP | 517516 B1 | 12/1999 |
| EP | 671626 B1 | 1/2000 |
| EP | 918984 B1 | 6/2001 |
| EP | 901620 B1 | 1/2002 |
| EP | 783683 B1 | 4/2004 |
| EP | 1413876 A2 | 4/2004 |
| EP | 901623 B1 | 6/2004 |
| EP | 1441217 A2 | 7/2004 |
| EP | 1315968 B1 | 2/2008 |
| EP | 1635177 B1 | 7/2008 |
| EP | 2154128 B1 | 12/2010 |
| EP | 2144947 B1 | 3/2011 |
| EP | 1356291 B1 | 5/2011 |
| EP | 2172503 B1 | 7/2011 |
| GB | 2377492 A | 1/2003 |
| JP | H11-281647 A | 10/1999 |
| JP | 2007101327 A | 4/2007 |
| JP | 2008513782 A | 5/2008 |
| JP | 2010160087 A | 7/2010 |
| WO | WO 94/18544 A1 | 8/1994 |
| WO | WO 94/27137 A2 | 11/1994 |
| WO | WO95/14225 A1 | 5/1995 |
| WO | WO 95/33197 A1 | 12/1995 |
| WO | WO 96/26432 A1 | 8/1996 |
| WO | WO97/35176 A1 | 9/1997 |
| WO | WO 97/35181 A1 | 9/1997 |
| WO | WO 97/35203 A1 | 9/1997 |
| WO | WO 97/39370 A1 | 10/1997 |
| WO | WO 99/14594 A1 | 3/1999 |
| WO | WO 99/45354 A2 | 9/1999 |
| WO | WO01/55691 A2 | 8/2001 |
| WO | WO02/37148 A2 | 5/2002 |
| WO | WO02/40998 A2 | 5/2002 |
| WO | WO 02/46756 A1 | 6/2002 |
| WO | WO 02/066983 A2 | 8/2002 |
| WO | WO 03/006625 A2 | 1/2003 |
| WO | WO03/021253 A2 | 3/2003 |
| WO | WO04/013616 A | 2/2004 |
| WO | WO 04/020987 A1 | 3/2004 |
| WO | WO04/23142 A1 | 3/2004 |
| WO | WO04/023143 A2 | 3/2004 |
| WO | WO 05/043139 A1 | 5/2005 |
| WO | WO 05/084367 A2 | 9/2005 |
| WO | WO 06/135782 A2 | 12/2006 |
| WO | WO 2007/070869 A2 | 6/2007 |
| WO | WO 2007/094817 A2 | 8/2007 |
| WO | WO 2007/123763 A2 | 11/2007 |
| WO | WO 2008/069973 A2 | 6/2008 |
| WO | WO2010/030251 A2 | 3/2010 |
| WO | WO2012/033466 A1 | 3/2012 |

OTHER PUBLICATIONS

Batzer et al.; Enhanced evolutionary PCR using Oligonucleotides with Inosine at the 3'-terminus; Nucleic Acid Res.; vol. 19; No. 18; p. 5081; Jul. 1991.

Bieche et al.; Quantitation of MYC Gene Expression in Sporadic Breast Tumors with a Real-time Reverse Transcription-PCR Assay; Cancer Res: vol. 59, No. 12, pp. 2759-2765; Jun. 1999.

Burgess et al.; A New Photolabile Protecting Group for Nucleotides; Abstracts of Papers Part 2.; 211th ACS National Meeting, American Chemical Society; New Orleans, LA; Mar. 24-28, 1996.

Chee et al.; Accessing Genetic Information with High Density DNA Arrays; Science; vol. 274, pp. 610-614; Oct. 1996.

(56) References Cited

OTHER PUBLICATIONS

Herron et al.; Orientation and Activity of Immobilized antibodies In: Biopolymers at Interfaces, 2nd Edition; Surfacant Science Series; Marcel Dekker, New York; vol. 110, pp. 115-163; Jan. 2003.

Herron et al.; Planar Waveguide Biosensors for Point-of-Care Clinical and Molecular Diagnositics In: Fluorescence Sensors and Biosensors; R. B. Thompson, Ed. CRC Press Taylor & Francis Group; Boca Raton, FL; pp. 283-332; Dec. 2005.

Hutchison, Clyde A.; DNA sequencing: bench to bedside and beyond; Nucleic Acid Res.; vol. 35; No. 18; pp. 6227-6237; Sep. 2007.

Innis et al.; PCP Protocols: A Guide to Methods and Applications; Elsevier Science & Technology; Jan. 1990.

Kaplan et al.;Rapid photolytic release of adenosine 5'-triphosphate from a protected analog: utilization by the sodium:potassium pump of human red blood ghost cells; Biochemistry; vol. 17; pp. 1929-1935; May 1978.

Kreuzer et al.; LightCycler Technology for the Quantitation of BCR/ABL Fusion Transcripts; Cancer Res.; vol. 59; No. 13; pp. 3171-3174; Jul. 1999.

Kulagina et al.; Antimicrobial peptides as new recognition molecules for screening challenging species; (Author Manuscript) Sens. Actuators B. chem.; vol. 121 (1); pp. 150-157; Jan. 2007.

Laurendeau et al.; TaqMan PCR-based gene dosage assay for predictive testing in individuals from a cancer family with INK4 locus haploinsufficiency; Clin Chem; vol. 45; No. 7; pp. 982-986; May 1999.

Levene et al.; Zero-Mode Waveguides for Single-Molecule Analysis at High Concentrations; Science; vol. 299; pp. 682-686; Jan. 31, 2003.

Lockhart et al.; Expression monitoring by hybridization to high-density oligonucleotide arrays; Nature Biotechnology; vol. 14; pp. 1675-1680; Dec. 1996.

McCray et al.; A new approach to time-resolved studies of ATP-requiring biological systems; laser flash photolysis of caged ATP; Proc. Natl. Acad. Sci. USA; vol. 77; No. 12; pp. 7237-7241; Dec. 1980.

Metzker et al.; Termination of DNA synthesis by novel 3'-modified-deoxyribonucleoside 5'-triphosphates; Nucleic Acids Res.; vol. 22; No. 20; pp. 4259-4267; Oct. 1994.

Ohtsuka et al.; An alternative approach to deoxyoligonucleotides as hybridization probes by insertion of deoxyinosine at ambiguous codon positions; J. Biol. Chem; vol. 260; pp. 2605-2608; Mar. 1985.

Pillai, Rajasekharan V.N.; V.N.; Photoremovable Protecting Groups in Organic Synthesis ; Synthesis; 1980(1); pp. 1-26; Jan. 1980.

Plowman et al.; Femtomolar Sensitivity using a channel-etched Thin Film Waveguide Fluoroimmunosensor; Biosensors & Bioelectronics; vol. 11(1-2); pp. 149-160; Jan. 1996.

Rossolini et al.; Use of deoxyinosine-containing primers vs degenerate primers for polymerase chain reaction based on ambiguous sequence imformation; Mol. Cell. Probes.; vol. 8; pp. 91-98; Jun. 1994.

Saizieu et al.; Bacterial transcript imaging by hybridization of total RNA to oligonucleotide arrays; Nat Biotechnol; vol. 16; No. 1; pp. 45-48; Jan. 1998.

Sun et al.; Synthesis of Novel Flourinated Coumarins: Excellent UV-Light Excitable Flourencent Dyes: Bioorganic & Med. Letters; vol. 8; No. 22; pp. 3107-3110; Nov. 1998.

Xu et al.; Protein and chemical microarrays—powerful tools for proteomics; J Biomed Biotechnol; vol. 2003(5); pp. 257-266; Dec. 2003.

Zehavi et al.; J. Light-sensitive glycosides. I. 6-nytroveratryl .beta.-D-glucopyranoside and 2-nitrobenzyl beta.-D-glucopyranoside; J. Organic Chem.; vol. 37(14); pp. 2281-2285; Jul. 1972.

Zourob et al.; Principles of bacterial detection: Biosensors, Recognition Receptors and microsystems; Eds., Springer Science and Business Media, NY; pp. 178-180; Jun. 2008.

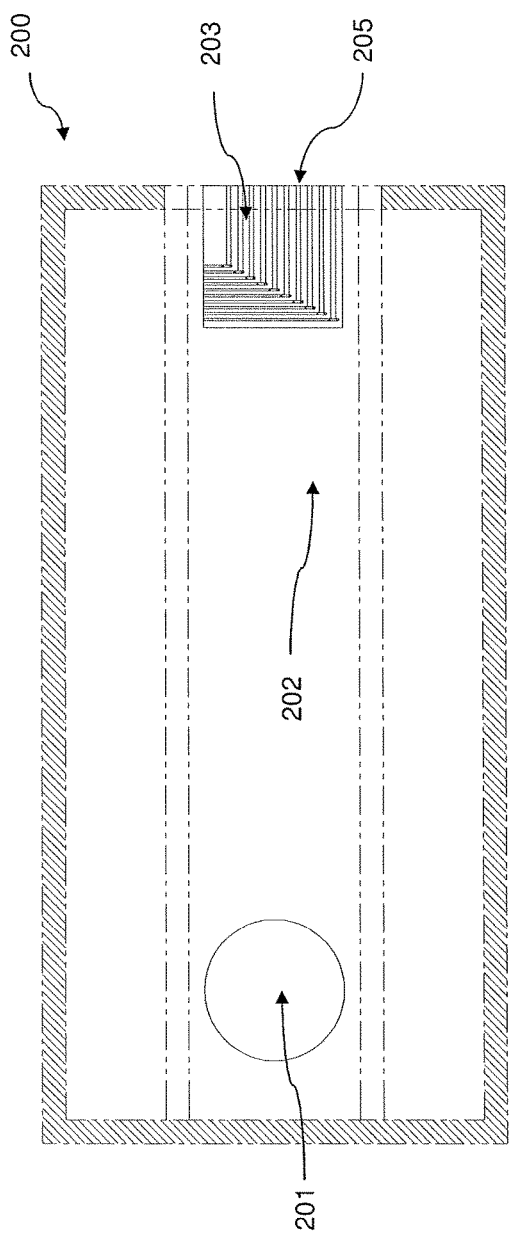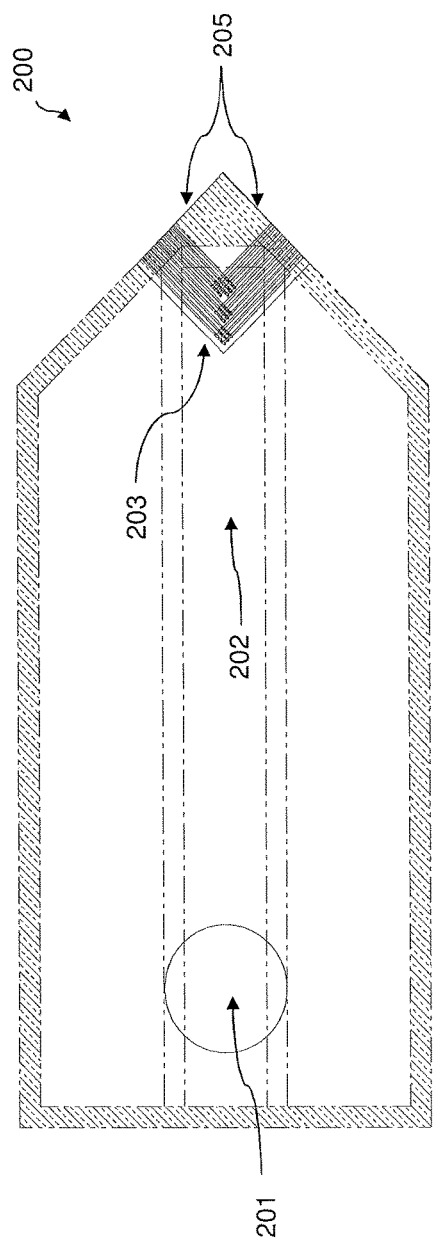
FIG. 2A
FIG. 2B

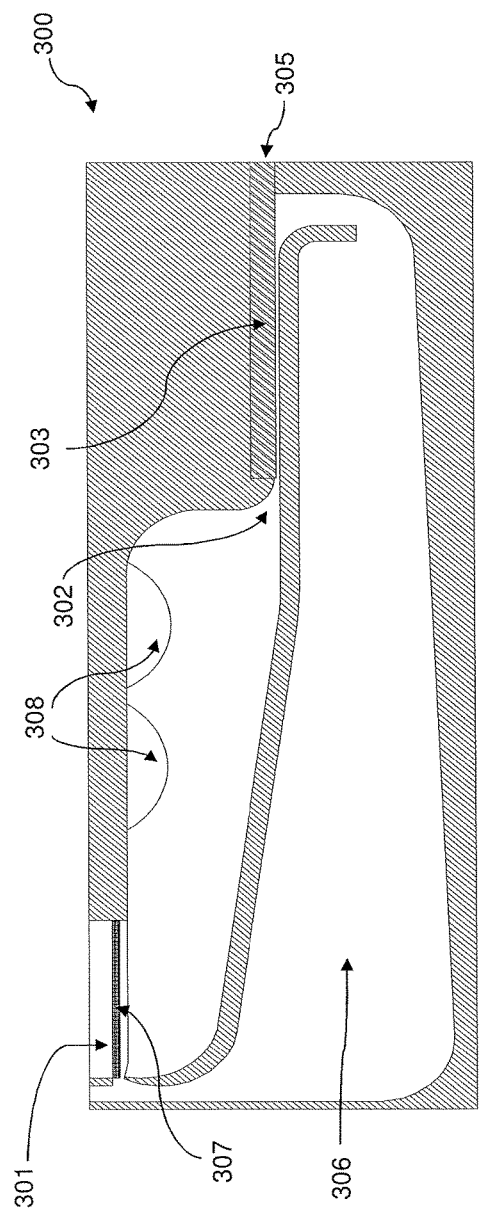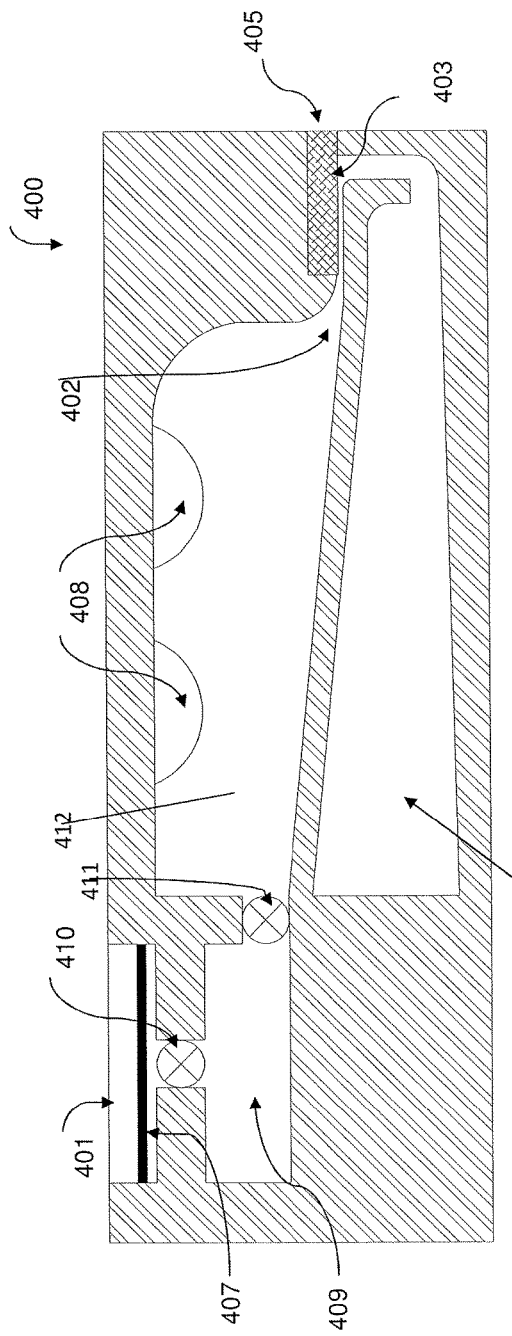

PARTIALLY ENCAPSULATED WAVEGUIDE BASED SENSING CHIPS, SYSTEMS AND METHODS OF USE

CROSS REFERENCE TO RELATED APPLICATIONS

This application claims priority to U.S. Provisional Patent Application No. 62/030,473, filed Jul. 29, 2014 and titled "PARTIALLY ENCAPSULATED WAVEGUIDE BASED SENSING CHIPS, SYSTEMS AND METHODS OF USE," the complete disclosure of which is herein incorporated by reference in its entirety.

This application may also be related to U.S. patent application Ser. No. 14/194,437, filed on Feb. 28, 2014, the complete disclosure of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates to partially-encapsulated waveguide-based sensing chips for use in bio-sensing applications.

BACKGROUND

The use of optical waveguides in their different forms has become prevalent across markets and applications. Optical waveguides in the form of optical fibers are the most common means for transporting telecommunication and data-communication signals across oceans, continents and all the way to individual homes. In medicine, optical fibers are widely used for endoscopy, in vivo and in vitro diagnostics, surgery and many other applications. Optical fibers are also used as part of sensing systems for monitoring temperature and stress on large infrastructure projects (e.g., bridges) and within deep oil wells.

A different type of optical waveguide is created on flat-round wafers (usually made of silicon) using technologies similar to the ones used for creating electronic "chips". These "planar waveguides" form part of optical chips also known as Planar Lightwave Circuits (PLC). PLC chips are more sophisticated than bare optical fibers and are used to manipulate light by splitting its power, switching it to different paths, time modulating it or dispersing it to its different components (i.e., wavelengths).

The use of waveguide chips in bio-sensing applications has been described in U.S. Pat. No. 7,951,583 B2, U.S. Pat. No. 8,187,866 B2 and U.S. Pat. No. 8,288,157 B2. In these type of application it is advantageous to have the sensing chip partially encapsulated in a cartridge (preferably low-cost) or housing which serves to conveniently handle the small chip, accept the biological sample to be tested, store reagents needed to run the test, introduce the sample and reagents to the sensing chip and allow easy insertion of the sensing chip into the optical reader.

SUMMARY OF THE DISCLOSURE

In general, described herein are apparatuses (including systems and devices, such as cartridges) and methods for detecting level(s) of analyte from a sample, such as a blood sample. These apparatus may include a sensing chip within a housing; the sensing chip may include a sensing surface, one or more excitation waveguides and one or more collection waveguides. In generally, these sensing chips are only partially encapsulated within the housing ("cartridge"), so that one or more side/edge regions of the chip are exposed, and in particular, so that the edge/side region of the chip including the ends of one or more excitation waveguides and a plurality of collection waveguides. A sensing surface on the chip, as well as fluidic handling (waste, valves, mixing chambers, etc.) may be encapsulated with the housing, as well as, in some variations, the bulk of the sensing chip.

The chip may be arranged so that excitation light applied to a side (e.g., an edge) region of the chip can travel down a (e.g., planar) waveguide in the chip to excite a molecule (e.g., light-sensitive analyte or a detection moiety bound to the analyte) on the sensing surface so that it emits light which is then passed through a collection (e.g., planar) waveguide for detection from a side region (e.g., edge) region of the chip. The side region(s) may be formed in part by an exposed portion of the excitation waveguide and the collection waveguides.

These partially-encapsulated chips typically mate with an optical reader that can both apply light (excitation light) and receive sensed (collected) light as binding of an analyte from a sample occurs on the sensing surface of the chip; the binding detected may be used to determine the concentration of analyte in the sample.

Any of the partially-encapsulated chips described herein may also be particularly configured so that at least one of the sub-regions of the binding surface (optical sensing sites) is configured as an alignment optical sensing site/alignment waveguide that is coated with a florescent marker (that may be a soluble florescent marker) to allow fine alignment with the partially-enclosed chip after it has been inserted into an optical reader. Alignment optical sensing sites coated with a fluid (e.g., sample fluid) soluble florescent marker are of particular use, as these sensing sites may be used both to physically align an optical reading head with the exposed ends of the excitation and collection waveguides, but it may also be used to indicate when fluid sample has contacted the sensing surface (optical sensing sties) and may be tracked to monitor the release/wash-away of the florescent marker by the fluid sample, which may be used to further calibrate the system.

In general, light may be coupled between the sensing surface and/or collection waveguide and/or excitation waveguide by evanescent coupling. In addition, the sensing chip may be arranged in the cartridge so that the sensing surface is exposed to a flow channel connected to a sample inlet port; the flow channel may also connect to a waste reservoir for holding the applied fluid. The cartridge may include additional components such as a filter (e.g., for removing cells), a metering chamber, an outlet port, etc. In addition, the chip may be held within the cartridge so the optical coupling regions (the side regions providing access to the excitation waveguide and the collection waveguide) communicate with, or form a part of, a side region of the cartridge for optically coupling light into and out of the waveguides.

The cartridges may also include an alignment guide (e.g., notch, mark, keying) that aligns the optical coupling regions on the side(s) of the cartridge, which give access (and in some cases direct access) to the collection and excitation waveguides, with one or more optical heads for applying light to the excitation waveguide(s) and detecting light from the collection waveguide(s).

The optical reader systems described herein may therefore be adapted for use with the partially-encapsulated sensing chips described herein. For convenience, the partially-encapsulated sensing chips described herein may also be referred to as "cartridges" though it should be understood that the cartridge includes the sensing chip having one or more exposed edge regions that provide direct access to the excitation and collection waveguides. An optical reader system may therefore include a cartridge holding region (including alignment components for securing the partially-encapsulated sensing chip in alignment with one or more optical head. The optical reader may also include control elements (processors, software and/or hardware) for controlling the application and detecting of light to the exposed waveguides of the partially-encapsulated sensing chip. The control elements may also analyze the detected signals, and provide a user interface. The optical reader may also include one or more pumps, for applying and/or moving sample through the housing of the partially-encapsulated sensing chip, as well as one or more valves (or valve controls) and actuators.

For example, described herein are partially-encapsulated sensing chip for detecting a level of an analyte in a sample. The partially-encapsulated sensing chip may include: a housing; a fluidic input port on the housing for receiving the sample; a flow channel within the housing in fluid communication with the fluidic input port; a sensing chip within the housing, the sensing chip comprising an excitation waveguide exposed at a first side region of the chip, a collection waveguide exposed at a second side region of the chip, wherein the excitation waveguide and the collection waveguide are evanescently coupled, a sensing surface on, or optically coupled with, the excitation waveguide, wherein the sensing surface is in fluid communication with the flow channel, wherein the first side region couples at a first outer surface region of the housing for optically coupling with the excitation waveguide, and wherein the second side region couples at a second outer surface region of the housing for optical coupling with the collection waveguide; and a waste reservoir within the housing in fluid communication with the flow channel for receiving the sample from the flow channel.

A system for measuring the level of an analyte in a sample may include: a partially-encapsulated sensing chip comprising a housing, a fluidic input port on the housing for receiving the sample, a flow channel within the housing in fluid communication with the input fluidic port, a sensing chip within the housing, and a waste reservoir within the housing in fluid communication with the flow channel for receiving the sample from the flow channel, wherein the sensing chip comprises one or more excitation waveguides, one or more collection waveguides, a sensing surface, and one or more exposed optical coupling surfaces, the sensing surface in fluid communication with the flow channel; an optical reader configured to receive the partially-encapsulated sensing chip, the optical reader comprising an optical head configured to direct excitation light into the excitation waveguides and receive emission light from the collection waveguides, wherein the optical head is aligned with the one or more exposed optical coupling surfaces of the sensing chip.

Also described herein are methods of detecting the level of an analyte in a sample, the method comprising: applying a fluid sample to a fluidic input port of a housing of a partially-encapsulated sensing chip; passing the fluid sample against a sensing surface of a sensing chip within the housing; applying excitation light (from an optical head) to a first outer surface region of the housing of the partially-encapsulated sensing chip which is in optical communication through a first side region of the sensing chip to which an excitation waveguide is exposed, to direct excitation light to the excitation waveguide; exciting an indicator on the sensing surface with the excitation light so that it emits light in relation to the level of the analyte in the fluid sample; and detecting the emitted light from a collection waveguide from a second outer surface region of the housing of the partially-encapsulated sensing chip which is in optical communication through a second side region of the sensing chip to which the collection waveguide is exposed, wherein the sensing surface is not rinsed before detection.

In some embodiments, a partially-encapsulated sensing chip for detecting a level of an analyte in a sample is provided. The partially-encapsulated sensing chip can include a housing; a fluidic input port on the housing for receiving the sample; a flow channel within the housing in fluid communication with the fluidic input port; a sensing chip within the housing, the sensing chip including a sensing surface in fluid communication with the flow channel, an excitation waveguide extending through the sensing chip and exposed at a first side region of the chip, a collection waveguide extending through the sensing chip and exposed at a second side region of the chip, wherein the excitation waveguide and the collection waveguide cross and are evanescently coupled at an optical sensing site on the sensing surface, wherein the first side region is exposed at a first outer surface region of the housing for optically coupling directly with the excitation waveguide, and wherein the second side region is exposed at a second outer surface region of the housing for optical coupling directly with the collection waveguide; and a waste reservoir within the housing in fluid communication with the flow channel for receiving the sample from the flow channel.

In some embodiments, a partially-encapsulated sensing chip for detecting a level of an analyte in a sample is provided. The partially-encapsulated sensing chip can include a housing; a fluidic input port on the housing for receiving the sample; a flow channel within the housing in fluid communication with the fluidic input port; a sensing chip within the housing, the sensing chip including a sensing surface in fluid communication with the flow channel, an excitation waveguide extending through the sensing chip and exposed at a first side region of the chip, a plurality of collection waveguides extending through the sensing chip and exposed at a second side region of the chip, wherein the excitation waveguide and the collection waveguides cross and are evanescently coupled at optical sensing sites on the sensing surface, and an alignment optical sensing site formed at one or more of the optical sensing sites comprising a florescent marker on the optical sensing site; wherein the first side region is exposed at a first outer surface region of the housing for optically coupling with the excitation waveguide, and wherein the second side region is exposed at a second outer surface region of the housing for optical coupling with the collection waveguide; and a waste reservoir within the housing in fluid communication with the flow channel for receiving the sample from the flow channel.

In some embodiments, the florescent marker on the optical sensing site is water soluble and configured to be released from the alignment optical sensing site upon contact with an applied sample.

In some embodiments, the sensing surface faces away from the input fluidic port and towards the waste reservoir.

In some embodiments, the first side region and the second side region are adjacent to each other.

In some embodiments, the first side region is a first edge region.

In some embodiments, the second side region is a second edge region.

In some embodiments, the first and second outer surface regions form a single optical coupling region on an outer surface of the housing.

In some embodiments, the first outer surface region and the second outer surface region are on the same outer surface of the housing.

In some embodiments, the first outer surface region and the second outer surface region are on different outer surfaces of the housing.

In some embodiments, the partially-encapsulated sensing chip further includes a filter upstream of the flow channel for filtering debris and/or red blood cells from the sample before the sensing surface.

In some embodiments, the partially-encapsulated sensing chip further includes a chamber between the input fluidic port and the flow channel that comprises one or more reagent storage compartments.

In some embodiments, the partially-encapsulated sensing chip further includes a metering and mixing compartment, wherein the metering and mixing compartment has a predetermined volume.

In some embodiments, the partially-encapsulated sensing chip further includes a metering and mixing compartment having a predetermined volume, wherein the metering and mixing compartment comprises mixing beads.

In some embodiments, the partially-encapsulated sensing chip further includes a metering and mixing compartment having a predetermined volume, wherein the metering and mixing compartment comprises baffles.

In some embodiments, the partially-encapsulated sensing chip further includes an elastomer in areas adjacent to the flow channel which can be distended using an external actuator for closing the flow channel.

In some embodiments, the partially-encapsulated sensing chip further includes an opening in the housing that is configured to allow the external actuator to access the elastomer for distending the elastomer and closing the flow channel.

In some embodiments, the partially-encapsulated sensing chip further includes one or more openings in areas adjacent to the flow channel in the housing which can be in gaseous communication with an external pump and or an external valve for generating negative or positive pressure in the flow channel for pulling or pushing the sample.

In some embodiments, the partially-encapsulated sensing chip further includes a capillary channel configured to pull in the sample from the fluidic input port to the flow channel using capillary force.

In some embodiments, the capillary channel has a predetermined volume configured to precisely meter a predetermined volume of the sample.

In some embodiments, the capillary channel is configured for storing a reagent, metering the sample and mixing the reagent with the sample.

In some embodiments, a system for measuring the level of an analyte in a sample is provided. The system can include a partially-encapsulated sensing chip including a housing, a fluidic input port on the housing for receiving the sample, a flow channel within the housing in fluid communication with the input fluidic port, a sensing chip within the housing, and a waste reservoir within the housing in fluid communication with the flow channel for receiving the sample from the flow channel, wherein the sensing chip comprises one or more excitation waveguides, a plurality of collection waveguides, a sensing surface, and one or more exposed optical coupling surfaces, the sensing surface in fluid communication with the flow channel; an optical reader configured to receive the partially-encapsulated sensing chip, the optical reader including: an optical head configured to direct excitation light into the excitation waveguides and receive emission light from the collection waveguides, a controller configured to align the optical head with the sensing chip by causing the optical head to scan an outer surface of the housing to identify a collection waveguide that is optically coupled with an alignment optical sensing site formed on the sensing surface, the alignment optical sensing site including a soluble florescent marker.

In some embodiments, the optical reader further comprises one or more air pumps in air-flow communication with the flow channel through one or more openings in the housing for pulling and/or pushing the sample inside the housing.

In some embodiments, the system further includes an elastomer adjacent the flow channel, and wherein the optical reader further includes one or more mechanical actuators in communication with the elastomer through the one or more openings in the housing for closing and opening the flow-channel by distending the elastomer.

In some embodiments, the optical reader further comprises one or more mechanical actuators in communication with the housing for breaking and/or pushing dedicated parts of the housing for controlled activation of the sample flow within the housing.

In some embodiments, the optical reader further comprises an actuator configured to align the optical head and the one or more exposed optical coupling surfaces of the sensing chip.

In some embodiments, a method of detecting the level of an analyte in a sample is provided. The method can include applying a fluid sample to a fluidic input port of a partially-encapsulated sensing chip within a housing; passing the fluid sample against a sensing surface of a sensing chip within the housing; applying excitation light directly to an excitation waveguide that ends at a first side region of the sensing chip, wherein an end of the excitation waveguide is exposed through an opening at a first outer surface region of the housing, to direct excitation light to the excitation waveguide; exciting an indicator on the sensing surface with the excitation light so that it emits light in relation to the level of the analyte in the fluid sample; and detecting the emitted light from a collection waveguide of the sensing chip, wherein an end of the collection waveguide is exposed through the housing at a second outer surface region of the housing, and wherein the sensing surface is not rinsed before detection.

In some embodiments, the method further includes connecting the housing of the partially-encapsulated sensing chip into an optical reader using an alignment member on the housing, to secure the housing relative to the optical reader.

In some embodiments, the method further includes filtering the fluid sample within the housing.

In some embodiments, the method further includes aligning the first outer surface region of the housing with an optical head.

In some embodiments, the method further includes aligning the first outer surface region of the housing with an optical head by first scanning an outer surface of the housing with an optical head to determine the alignment offset for the optical head.

In some embodiments, the method further includes activation of one or more pumps and one or more actuators using a pre-defined sequence and timing for moving the sample within the housing, for filtering the sample, for metering the sample, for mixing the sample with the stored reagents, and for introducing the sample to the sensing surface of the chip.

In some embodiments, the method further includes detecting an alignment signal from an alignment optical sensing site before the addition of sample, wherein the alignment signal comprises a florescent marker coated on the sensing site.

BRIEF DESCRIPTION OF THE DRAWINGS

FIG. 2A is a schematic top view of an embodiment of a partially-encapsulated sensing chip showing an input fluidic port, a flow channel, a sensing chip, and one exposed edge of the sensing chip allowing optical coupling.

FIG. 2B is a schematic top view of another embodiment of a partially-encapsulated sensing chip showing an input fluidic port, a flow channel, a sensing chip, and two exposed edges of the sensing chip allowing optical coupling.

FIG. 3 is a schematic drawing of a partially-encapsulated sensing chip showing an input fluidic port, a flow channel, a sensing chip, an exposed edge of the sensing chip allowing optical coupling, a waste reservoir, a filtering component for filtering the sample, and two reagent storage compartments.

FIG. 4A is a schematic illustration of another example of a partially-encapsulated sensing chip, including a metering/mixing compartment and valves.

DETAILED DESCRIPTION

Figure 1A:
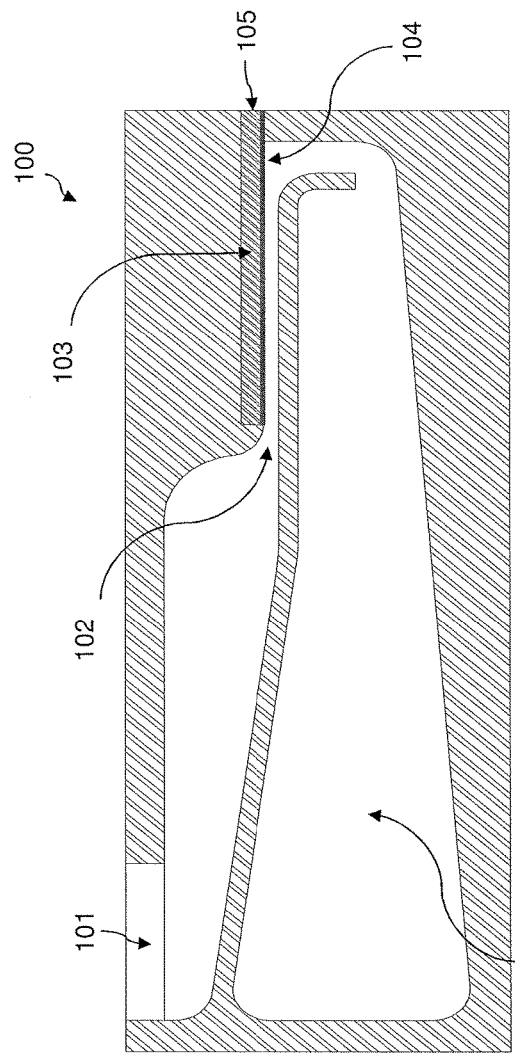
FIG. 1A is a schematic drawing of one embodiment of a partially-encapsulated sensing chip showing an input fluidic port, a flow channel, a sensing chip with a downward facing sensing surface, an exposed edge of the sensing chip allowing optical coupling, and a waste reservoir.

The apparatuses described herein typically include waveguide-based sensing chips that are adapted for use as part of a disposable, lightweight and reliable partially-encapsulated sensing chip (e.g., cartridge) for detecting an analyte from a fluid sample. These partially-encapsulated sensing chips can include various features and functions. For example, any of the partially-encapsulated sensing chips may encapsulate the sensing chip with waveguides in a housing while allowing optical interface to the chip along one or two of its edges. The housing with the sensing chip maybe mechanically aligned to an optical reader for optical coupling. The partially-encapsulated sensing chip may be pre-loaded and/or may store reagents or accept addition of reagents needed to run a test. The partially-encapsulated sensing chip may accept different volumes of the biological sample to be tested. The partially-encapsulated sensing chip may filter some parts of the biological sample (e.g. red blood cells), and/or may meter the (e.g., filtered) sample. In some variations the housing of the partially-encapsulated sensing chip may mix onboard reagents or the added reagents with the metered biological sample. The partially-encapsulated sensing chip may also be configured to introduce the mixed reagents and sample to the sensing chip. The partially-encapsulated sensing chip and/or the optical reader may control the timing of any of these steps or features, to allow monitoring of the assay for the detection of the analytes of interest.

In general, the cartridge partially houses or contains the sensing chip (e.g., leaving an edge or side region where the waveguides end exposed) and may provide a mechanism for mechanical alignment of the sensing chip for optical coupling to the optical reader. The cartridge (e.g., a housing portion of the partially-encapsulated sensing chip) typically has an input fluidic port for the introduction of the biological sample to be tested and reagents needed for the test. The cartridge may contain a variety of fluidic channels, and may optionally include valves and vents for manipulating the sample and/or reagent(s). The cartridge may include a filter for removing components of the sample, storage compartments (e.g. 'blisters') for storing dry or liquid reagents, and cavities that can be used to meter combine and mix the sample and the reagents to be used in the test. It may also contain a waste reservoir to where the reagents and sample can flow after being used. The cartridge allows a controlled flow of the reagents and the sample from the input fluidic port to the sensing areas on the waveguide chip, and further to the waste reservoir.

The cartridge typically also partially contains a sensing chip and may include one or more alignment features for mechanical alignment of the sensing chip for optical coupling to the optical reader. The cartridge has an input fluidic port for the introduction of reagents needed for the test and the sample to be tested. The cartridge may also contain one or several storage compartments able to store reagents in a dry or liquid form on board the partially-encapsulated sensing chip and a waste reservoir to where the reagents and the sample can flow after being used. The partially-encapsulated sensing chip and reader may allow the release of the reagents stored in the storage compartments in a controlled manner, mixing them with the reagents and sample introduced through the input fluidic port and flow to the sensing areas on waveguide chip and further to the waste reservoir.

As mentioned, in some variations, the partially-encapsulated sensing chip contains a filter to filter the sample to be tested after it enters the input fluidic port for the removal of components such as red-blood-cells, other types of cells and solid particulates. In embodiments, some reagents may be dried (e.g. lyophilized) on the sensing chip and/or along the flow-path of the sample/reagent. Upon introduction of a sample/reagent, the dried reagents may dissolve and mix with the added sample/reagent and the mix is available for the performance of the test.

The partially-encapsulated sensing chip may contain one or more chambers to measure and control the volume of sample or reagents. The measurement and control of the volume can be done before or after filtering, before or after mixing and before or after introducing to the sensing chip.

The partially-encapsulated sensing chip may contain a number of valves and/or vents, part of which can be passive or active, and the activator/activation mechanism (e.g. solenoids) may be part of the optical reader. The optical reader may contain one or more pumps that can be coupled to the partially-encapsulated sensing chip through dedicated ports to create negative or positive pressure for generating flow inside the housing of the partially-encapsulated sensing chip.

The sensing chip may be mounted inside the cartridge with its sensing surface facing any direction, including down, as illustrated in FIG. 1A. A flow-channel may be created between the sensing surface of the sensing chip and one surface of the housing of the partially-encapsulated sensing chip may be located adjacent to it at a predefined distance apart. The reagents/sample flowing through that flow-channel underneath the sensing chip may be contact with the sensing surface of the sensing chip, allowing the detection of the test targets. At the end of the flow-channel, the reagents/sample may flow to the waste reservoir.

Figure 1B:
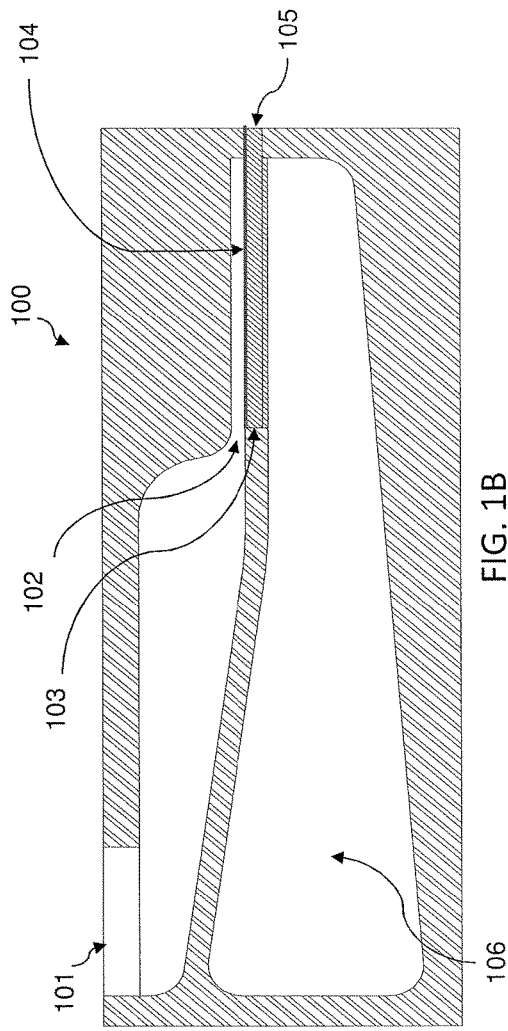
FIG. 1B is a schematic drawing of another embodiment of a partially-encapsulated sensing chip showing an input fluidic port, a flow channel, a sensing chip with an upward facing sensing surface, an exposed edge of the sensing chip allowing optical coupling, and a waste reservoir.

The sensing chip may be mounted inside the housing with its sensing surface facing up, as illustrated in FIG. 1B. A flow-channel is created between the sensing surface of the sensing chip and one surface of the housing placed adjacent to it at a predefined distance apart. The reagents/sample flowing through that flow-channel on-top the sensing chip may be in contact with the sensing surface of the sensing chip allowing the detection of the test targets. At the end of the flow-channel, the reagents/sample may flow to the waste reservoir.

Figure 1C:
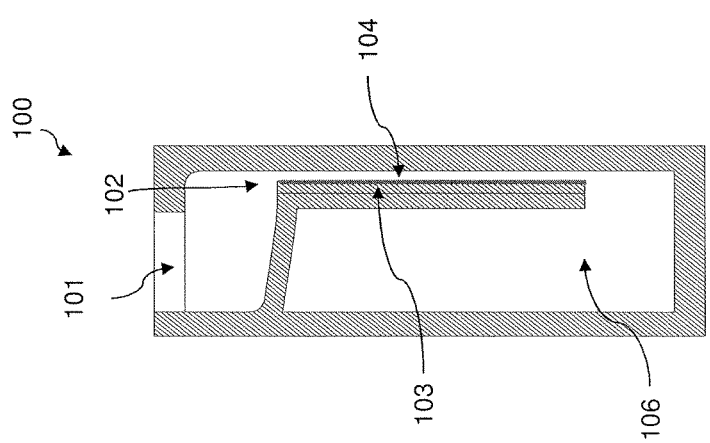
FIG. 1C is a schematic drawing of another embodiment of a partially-encapsulated sensing chip showing an input fluidic port, a flow channel, a sensing chip with a sideways facing sensing surface, and a waste reservoir.

The sensing chip may be mounted inside the housing with its sensing surface facing sideways, as illustrated in FIG. 1C. A flow-channel may be created between the sensing surface of the sensing chip and one surface of the housing placed adjacent to it at a predefined distance apart. The reagents/sample flowing through that flow-channel on the side of the sensing chip may be in contact with the sensing surface of the sensing chip allowing the detection of the test targets. At the end of the flow-channel, the reagents/sample may flow to the waste reservoir.

The flow through the flow-channel may be generated passively due to the gravitational force and/or the capillary force created in the flow-channel. Flow through the flow-channel may be generated actively using a small pump located in the optical reader and may couple through a dedicated port to the housing. The flow-channel can be wider than or narrower than the sensing chip.

The housing may contain an identifier (e.g., a partially-encapsulated sensing chip identifier or code) such as a bar-code or radio frequency identification (RFID) which can be used to store or communicate information about the partially-encapsulated sensing chip such as the type of test it is intended for, manufacturing and expiration dates, lot number and other batch related information. The bar-code can also contain a unique identification codes which can be connected with the sample/patient tested on it thus allowing record maintenance and traceability. The bar-code and/or RFID can also indicate to the optical reader which procedures and protocols to use for the assay contained in the housing.

Returning now to FIG. 1A, FIG. 1A illustrates an embodiment of a housing 100 with an input fluidic port 101 for introducing or inputting fluid into the housing 100, such as the sample, buffers, reagents, and the like. In general, the housing may have a form factor that matches a receptacle in optical reader. The input fluidic port 101 is in fluid communication with a flow channel 102 that passes along one or more sensing surfaces 104 of a sensing chip 103, which can have an exposed edge 105 for optical coupling to an optical reader. The flow channel 102 is also in fluid communication with a waste reservoir 106, which can be located below the flow channel 102 and sensing chip 103 so that gravity can be used to assist the fluid flow through the housing. In this embodiment, the sensing surface 104 of the sensing chip 103 is facing downwards and towards the waste reservoir 106. The housing 100 can also have a chamber between the input fluidic port 101 and flow channel 102 to hold up to a predetermined amount of sample and/or reagent. The volumes can be small (e.g., less than a microliter). For example, the loading volume may be between 5 and 0.1 microliters. The chambers described herein may be configured to hold this loading volume, or less.

Having a downwards-facing sensing surface 104 provides several advantages, including reducing the amount of precipitation or debris that settles on the sensing surface 104. As used herein, the directions "upwards," "downwards" and "sideways" refers to the orientation relative to gravity. Other potential advantages of a downwards-facing sensing surface may include improved flow dynamics over the surface of the sensing surface 104 and simplified construction of the flow channel 102. The flow channel 102 can run along the width of the sensing surface 104 from the proximal edge of the sensing surface 104 towards the distal edge of the sensing surface 104 before connecting with the waste reservoir 106. Since the sensing chip 103 is above both the flow channel 102 and the waste reservoir 106, the sensing chip 103 is not between the flow channel 102 and waste reservoir 106, and therefore does not interfere with the flow path between the flow channel 102 and waste reservoir 106.

In some embodiments, the sensing surface 104 of sensing chip 103 can be upwards facing, as illustrated in FIG. 1B. The construction of the housing 100 of the partially-encapsulated sensing chip can otherwise be similar to the embodiment disclosed in FIG. 1A, with the following changes. The sensing chip 103, which has a distal exposed edge 105 for optical coupling, can be located between the flow channel 102 and waster reservoir 106, with the sensing surface facing upwards. As shown, the sensing chip 103 is interposed between the flow channel 102 and the waste reservoir 106 in this cross-sectional view, meaning flow channel 102 may connect to the waste reservoir 106 along one or both sides of the sensing chip 103, or alternatively, through one or more holes, channels or slots in the sensing chip 103.

In some embodiments, the sensing surface 104 of the sensing chip 103 can face sideways as illustrated in FIG. 1C. The housing 100 can be oriented vertically with the input fluidic port 101 on top, and the flow channel 102 below the input fluidic port 101 and oriented vertically with the sensing surface 104 of the sensing chip 103 also oriented vertically and forming one side of the flow channel. The waste reservoir 106 can be located below both the flow channel 102 and the waste reservoir. This configuration, like the downwards facing sensing surface 104 configuration illustrated in FIG. 1A, also provides the advantages of reducing the amount of precipitation or debris that settles on the sensing surface 104, improved flow dynamics over the surface of the sensing surface 104, and simplified construction of the flow channel 102. In addition, all three embodiments disclosed in FIGS. 1a-1c can use gravity to assist in pulling the fluid through the housing from the input fluidic port 101, through the flow channel 102 and across the sensing surface 104, and to the waste reservoir 106.

FIGS. 2A and 2B illustrate top views of two embodiments of the housing 200 of the partially-encapsulated sensing chip that show the orientation and configuration of various sensing chips 203. The housing 200 can otherwise be compatible with any of the embodiments described herein, such as having an input fluidic port 201 and flow channel 202. In FIG. 2A, the sensing chip 203 has excitation waveguides and collection waveguides that terminate on a single exposed edge 205 of the sensing chip 203 for optical coupling. Since the waveguides terminate on a single exposed edge 205, the distal end of the housing 200 with the exposed edge 205 that interfaces with the optical reader can be a single face. In FIG. 2B, the sensing chip 203 has excitation waveguides that terminate on one exposed edge 205 and collection waveguides that terminate on another exposed edge 205, which can also be an adjacent edge. Since the waveguides terminate on two exposed edges 205, the distal end of the housing 200 with the exposed edges 205 can have two angled faces that are aligned with the exposed edges 205. For example, for a square sensing chip 203 with two adjacent exposed edges 205, the distal end of the housing 200 can be formed from two faces that meet at a right angle. For sensing chips 203 with other geometries, such as rhomboid, the two faces can meet at a matching angle, which can be obtuse or acute, depending on the sensing chip configuration.

FIG. 3 illustrates another embodiment of a partially-encapsulated sensing chip 300. The housing of the partially-encapsulated sensing chip 300 can have an input fluidic port 301, flow channel 302, sensing chip 303 with an exposed edge 305, and waste reservoir 306 as described herein in various embodiments. For example, the sensing chip 303 can be downwards facing as shown, or can be upwards facing or sideways facing as described in other embodiments. In addition to these previously described components, the partially-encapsulated sensing chip 300 can have a filtering component 307 for filtering the sample as it is introduced into the housing 300. For example, the filtering component 307 can be placed across the input fluid port 301 to filter out debris, particulates, and/or cells such as blood cells, and prevent this material from clogging the flow channel 302 and/or interfering with the sensing chip 303. In addition, the housing 300 can have a sample chamber with one or more reagent storage compartments 308 that can release various reagents after the sample is introduced to the sample chamber. In some embodiments, the housing 300 can have 1, 2, 3, 4, 5, or more reagent storage compartments 308. The reagent storage compartments 308 can be designed to release reagents substantially simultaneously or sequentially, depending on the requirements of the assay. In some embodiments, the reagent storage compartments 308 can be made of a degradable or dissolvable polymer that breaks down when in contact with water or the sample.

FIG. 4A illustrates another embodiment of a partially-encapsulated sensing chip 400 that can have an additional metering and mixing compartment 409. In some variations, the metering and mixing compartment(s) 409, 412 are separate, while in some variations the metering and mixing compartments are integrated into a single compartment. As illustrated, the metering/mixing compartment(s) could include one or more reagents, such as lyophilized reagents, as described in more detail below. The reagents may be held within the compartment until fluid (e.g., sample fluid) is added. For example, fluid pressure may be applied to push or pull fluid (including sample fluid) into the compartment and allow mixing with the loaded reagents. Suction (negative pressure) may be applied at a port (not shown) such as an exit port, and/or the entrance port to pull fluid into or out of the chamber; similarly positive pressure may be applied to push fluid into and out of the chamber. The housing may include ports (e.g., venting ports) that include a membrane allowing air to flow in/out but preventing liquid (e.g., sample) from flowing out.

The housing of the partially-encapsulated sensing chip 400 can have the same or similar components as described herein in various embodiments, including an input fluidic port 401, a flow channel 402, a sensing chip 403 with a sensing surface exposed to the flow channel 402 and one or more exposed edges 405 for optical coupling, a waste reservoir 406, a filtering component 407, and one or more reagent storage compartments 408. In addition to these components, the housing 400 can have a metering and mixing compartment 409 for controlling the amount of sample and other fluids entering the housing 400.

A metering and mixing compartment 409 can be located between the input fluidic port 401 and the chamber with the reagent storage compartments 408, and can have one or more valves 410, 411 for controlling fluid entry into the metering and mixing compartment 409 and fluid exit from the metering and mixing compartment 409. For example, an inlet valve can be opened while leaving the outlet valve closed to fill the metering and mixing compartment 409. Once the fluid has filled the metering and mixing compartment 409, the inlet valve can be closed and the outlet valve can be opened to introduce the metered fluid to the rest of the housing 400.

Pre-loaded components such as reagents (e.g., antibodies, labeled antibodies, blocking agents, buffering agents, etc.) can be included in a dissolvable ('bubble') or lyophilized form that is made active when the sample (or a filtered version of the sample) is added. In FIG. 4A, for example, a sample added into the input port 401 may be drawn into the metering compartment 409, e.g., by pulling sample into the metering compartment with the loading valve 410 opened, but an exit valve 411 closed. Once loaded (which may be determined by time, or by actively (e.g., by electrical resistivity) sensing the fluid level in the metering chamber 409, the loading valve 410 may be closed, the exit valve 411 opened, and pressure (positive or negative) applied to move the fluid into the mixing chamber 412. Venting ports (not shown) may be included, as mentioned above. The mixing chamber may be the same size as the metering chamber, larger, or smaller. The mixing may be performed passively or actively (e.g., by applying alternating positive and negative pressure).

In some embodiments, the inlet valve can be located between the filtering component 407 and the metering and mixing compartment 409, while the outlet valve can be located between the metering and mixing compartment 409 and the chamber holding the reagent storage compartments 408. The size and volume of the metering and mixing compartment can be used to control the metering of the fluid. In addition, mixing beads and/or baffles can be placed within the metering and mixing compartment 409 as well as the chamber storing the reagent storage compartments 408 to promote mixing of the fluid, which can include the sample, buffers and reagents. Precise and reliable metering of the sample with the reagents is important to allow quantification of an analyte in the sample.

In some embodiments, the metering and mixing compartment 409 can be integrated with the chamber storing the reagent storage compartments 408. An inlet valve can be located between filtering component 407 and the metering and mixing compartment 409 and an outlet valve can be located between the metering and mixing compartment 409 and the flow channel 402 that runs across the sensing surface of the sensing chip 403. Thus, the metering and mixing compartment 409 can also contain the reagent storage compartments 408. In addition, the metering and mixing compartment 409 can include baffles and/or mixing beads to promote mixing of the sample with the reagents.

Figure 4B:
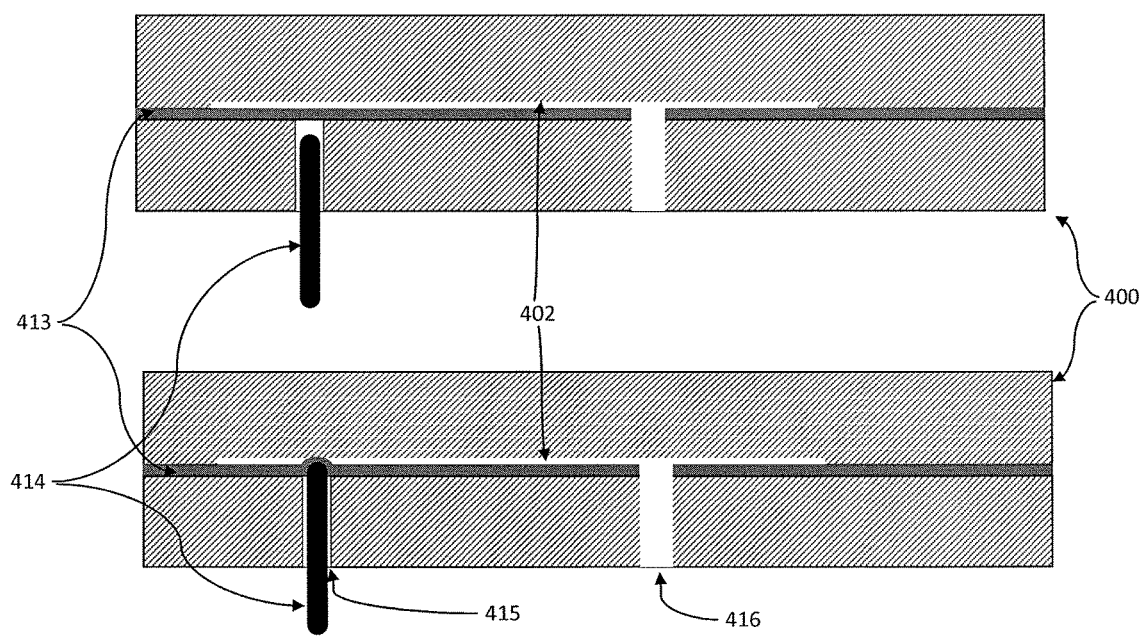
FIG. 4B is a schematic illustration of one embodiment of a cartridge with a flow channel that can be opened and closed using an actuator.

FIG. 4B illustrates one embodiment of a cross sectional view of a housing/cartridge 400 showing a flow channel 402 lined with an elastomer 413 and an actuator 414 which can be inserted through an opening 415 in the housing 400 to distend the elastomer 413 and reversibly seal the flow channel 402. In some embodiments, the actuator 414 can be a mechanical actuator such as a rod, piston or pin. In other embodiments, the actuator 414 can be a hydraulic actuator such as a pressurized fluid or gas. The actuator 414 is used to pinch or distend the elastomer 413 which reversibly closes or blocks the flow channel 402. Flow in the flow channel 402 can be restored by retracting or depressurizing the actuator 414. In some embodiments, a second opening 416 in the housing can be in fluidic/gaseous communication with an external air-pump or fluid pump for creating negative or positive pressure through a cut in elastomer 413 for pulling or pushing liquid in flow channel 402. In other embodiments, the second opening 416 can be in fluidic/gaseous communication with a negative pressure source and a positive pressure source via a valve.

Figure 4C:
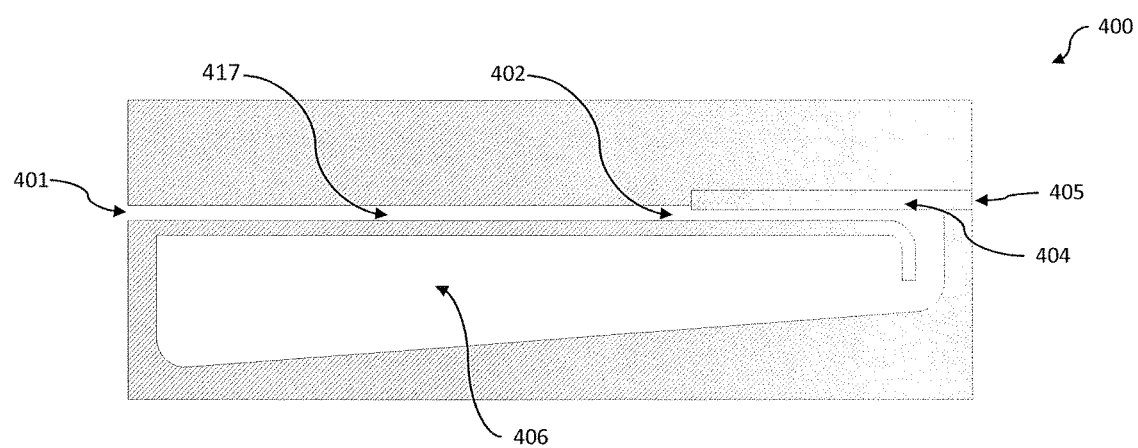
FIG. 4C is a schematic illustration of another embodiment of a cartridge with a capillary channel that can pull a predetermined and/or precise volume of liquid into the cartridge through capillary force and deliver the liquid to a flow channel.

FIG. 4C is a schematic illustration of another embodiment of a cartridge with a capillary channel that can pull a predetermined and/or precise volume of liquid into the cartridge through capillary force and deliver the liquid to a flow channel. A cross sectional view of the housing/cartridge 400 shows a flow channel 402, sensing chip 404 having an exposed optical coupling surface 405, and a waste reservoir 406. An input port 401 which is connected to and/or in fluid communication with the flow channel 402 through a thin capillary channel 417. The capillary channel 417 can pull a predetermined and/or precise volume of liquid through capillary force to deliver it to the flow channel 402. The volume of fluid pulled through the capillary channel can be controlled by the controlling the size of the capillary channel. For example, the capillary channel 417 can have a volume range between about 1 micro-liter to 250 micro-liters. In some embodiments, the volume of the capillary channel can be approximately equal to the volume of the sample in a one to one relationship. However, in some embodiments, only a small portion of the sample may be delivered to the sensing chip, such as less than 5, 10, 15, or 20 percent of the sample.

In some embodiments, the actuators can be in communication with the housing for breaking and/or pushing dedicated parts of the housing for controlled activation of the sample flow within the housing. For example, a reagent can be injected into the flow channel, the capillary channel, or a mixing chamber using a mechanical actuator. The reagent can be stored in a reagent chamber or depot than can be dispensed by advancing or retracting the actuator. In some embodiments, the flow through the one or more channels and other parts in the housing can be controlled by manipulating the actuators. In addition, one or more pumps can be used to also control the flow within the housing. In some embodiments, the activation of the pumps and actuators can be done in a predetermined sequence in order to move the sample within the housing, filter the sample, meter the sample, mix the sample with the stored reagents, and introduce the sample or part of the sample to the sensing surface of the chip.

Figure 5:
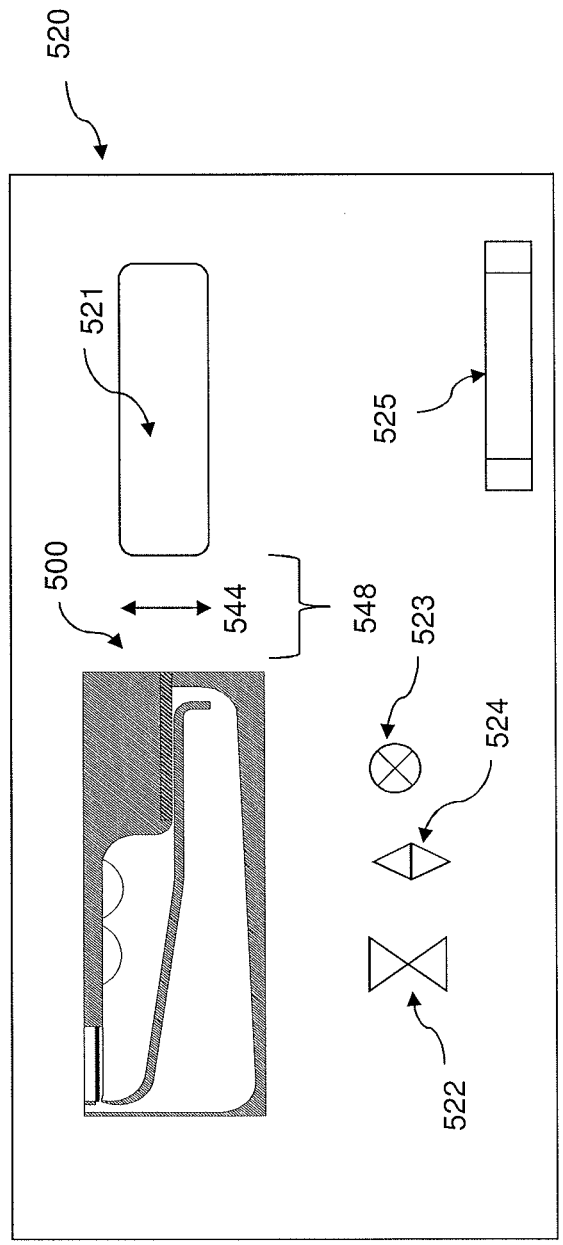
FIG. 5 is a schematic drawing of an embodiment of an optical reader system including a partially-encapsulated sensing chip, an optical head, a pump, a valve, an actuator, and the control electronics.

FIG. 5 is a schematic drawing that shows a partially-encapsulated sensing chip 500 operatively connected with an optical reader system 520. The optical reader system 520 can have an optical head 521 that is designed to interface with the exposed edge(s) of the sensing chip in the housing 500. The optical head 521 can provide excitation light to the excitation waveguides on the sensing chip and receive light emissions from the collection waveguides on the sensing chip. In general, the housing with the sensing chip is held securely in the optical reader. The reader may include a lock to engage the housing of the partially-encapsulated sensing chip and hold it secure (e.g., fixed relative to at least a portion of the optical reader). The housing may also include one or more orientation guides, including shaped or keyed housing regions that engage with the optical reader. For example, a housing may include a notch or more than one notch that engages a housing holder in the optical reader system and locks the housing and partially-encapsulated sensing chip in place. The lock may be latched so that the housing cannot be pulled loose or removed until after the reading has been performed or until the system otherwise releases it. The partially-encapsulated sensing chip holder may also hold the housing of the partially-encapsulated sensing chip in position so that the optical head component 521 may be scanned relative to the exposed ends of the waveguides at a side (e.g., edge) of the housing. In general, the waveguides must be exposed at a side (edge) of the housing so that there is an air gap between the waveguides and the light source of the optical head.

As mentioned above, the optical reader system 520 can include a pump 522 for pushing/pulling fluid through the housing of the partially-encapsulated sensing chip 500, and one or more pressure actuators for one or more of the valves 523 for controlling the flow of fluid through the cartridge by controlling the pressure (e.g., suction) provided by the pump 522, and a motor actuator 524 (e.g., a stepper motor) for aligning the partially-encapsulated sensing chip 500 with the optical head 521, and control electronics for controlling the operation of the optical head, 521, pump 522, valve(s) 523, and actuator 524.

For example, in operation, a partially-encapsulated sensing chip may be only roughly aligned when placed (manually) into the reader. A partially-encapsulated sensing chip holder may hold the partially-encapsulated sensing chip in the reader so that the distance between the partially-encapsulated sensing chip and the optical head 521 is approximately correct. More precise alignment (and therefore more precise tolerances on the partially-encapsulated sensing chip) are not necessary, as the optical head may be scanned to precisely identify the locations of the individual waveguides for reading. In particular, the optical head may be scanned from side to the other (scanning along the length of the partially-encapsulated sensing chip edge) and similarly scanned up/down (scanning along the thickness of the housing of the partially-encapsulated sensing chip). As described in greater detail below (in reference to FIG. 7A-7F), the partially-encapsulated sensing chip (e.g., housing) may be pre-loaded with a positive channel on which one optical sensing site of the sensing surface that is pre-loaded with an excitable marker (e.g., fluorophore) that can be excited through the excitation waveguide and sensed from a predefined collection waveguide corresponding to the optical sensing site. The marker may be dissolvable with the addition of the sample (e.g., blood, bodily fluid, etc.), allowing the time course of release of the marker (and therefore a change in the signal) to indicate both the start of the application of sample to the sensing surface as well as a control time course for sensing.

In some variations the optical head include a fiber array that couples to the waveguides (across an air gap), and is scanned up and down while moving forward/backward (e.g., scanning in both x (up/down) and y (backwards/forwards); the partially-encapsulated sensing chip is held a fixed z distance (air gap) from the scanning optical head.

The controller may control scanning of the head to align the head with the partially-encapsulated sensing chip so that he controller confirms when the partially-encapsulated sensing chip (and particularly the exposed ends of the waveguides for a particular device) are in position to begin monitoring the surface activity of the waveguide. Coupling can be detected from any of the sensing sites on the sensing surface of the chip (e.g., the optical sensing sites above the intersection of the excitation and collection waveguides). The head may be scanned while applying excitation to one or both excitation waveguides until a peak is identified from one or more of the collection waveguides. In general, proper coupling of the head results in an aligned excitation channel and collection waveguide, which can be detected as a peak from a collection waveguide when scanning. Scanning my by dynamic or performed in increments (e.g., 1-50 µm step increments) and monitored for peak signal. In some variations the entire height and width of the cartridge side (edge) may be scanned, and examined to identify the location of the peak, to determine the offset. Once the controller determines this peak and calculates the offset, the system may be operated to begin the test, and monitor the collection waveguides (e.g., starting fluid/sample flowing across the sensing surface after mixing appropriately). The use of the control optical sensing site with the known (and dissolvable marker) may be particular helpful in aligning the partially-encapsulated sensing chip relative to the reader, however, even without a marker, proper alignment to a collection waveguide may be identified by a change in the relative background of the sensed signal; aligning with a collection waveguide typically results in a peak showing coupling.

In any of the partially-encapsulated sensing chip variations described herein a chip may include one or more optical sensing sites (wells) onto which a predetermined, and typically soluble, marker (e.g., fluorophore) is printed. The collection waveguide corresponding to the predetermined marker may be referred to as an alignment channel. The alignment channel may be dedicated for use as an alignment channel. In some variation it may also be a testing channel (waveguide and optical sensing site). For example, the optical sensing site may also be coated with a binding partner (e.g., antibody) for the analyte being examined.

Other positive control channels (optical sensing sites) may also be included, including positive controls for the binding reaction. For example, an optical sensing site may be coated with a binding partner for a control analyte that is included (e.g., in the lyophilized or otherwise included reagents) in the partially-encapsulated sensing chip. The control channels may be monitored to examine the binding kinetics of the control molecule which should be predefined (known) by the controller and may therefore be used to adjust/correct the signal from the sample sites (optical sensing sites).

As mentioned, in operation, the distance between the chip (exposed waveguides on the side/edge of the housing of the partially-encapsulated sensing chip) and the optical head may be mechanically defined by the partially-encapsulated sensing chip holder. For example, the clamp holding the partially-encapsulated sensing chip within the system may have a mechanic actuator (e.g., plunger) that confirms that the spacing distance between the partially-encapsulated sensing chip and the optical head is within the desired range (limits or tolerances). Scanning may be used to position in the vertical (up/down or x direction) and horizontal (side to side or y direction). For example, the waveguide in a sensing chip may be approximately 150 nm thick, and the alignment controller (e.g., a piezo actuator or a stepper motor) controlled by the system controller may provide scanning in both x and y. For example, with reference to FIG. 5, the partially-encapsulated sensing chip holder may hold the partially-encapsulated sensing chip a fixed distance 548 from the scanning head (in z); the optical head 521 may be scanned in x 544 (e.g., up/down in the figure) and in y (in/out of the page in FIG. 5). For example, if the head may scan a total of 5 microns in the y direction (in/out of the page) and a total of 200 um in the x direction (up/down), repeatedly (e.g., to cover a complete length of the exposed edge of the chip in the housing (e.g., 100 um) to detect signal and determine the alignment. The holder may therefore allow the partially-encapsulated sensing chip to be held a fixed distance from the scanning head, and prevent rotation. The scanning optical head may include, for example, parallel channels for reading from multiple collection waveguides either simultaneously or sequentially (e.g., the optical head may include a CCD chip with different areas coupled to different outputs). For example, in some variations the optical head is matched to the sensing chip and includes x outputs (where x is the number of excitation waveguides or a fraction, e.g., ½, ⅓, etc., thereof) and y inputs (where y is the number of collection waveguides or a fraction thereof). In one variation having two excitation and 8 collection waveguides with 16 optical sensing sites, the optical head may include 2 outputs (excitation outputs) and 8 inputs (collection waveguide inputs), so there are a total of 16 channels for measuring. In some variations the sensing chip includes 1 excitation and 8 collection waveguides (for a total of 8 channels) and the optical head may be matched accordingly. In some variations the optical sensing chip includes 2 excitation waveguides and 8 collection waveguides; in some variations the optical sensing chip includes 4 excitation waveguides and 8 collection waveguides (see, e.g., FIGS. 7A and 7D, respectively). The alignment step may be performed after the partially-encapsulated sensing chip (loaded with sample) is inserted into the reader, and before sample is applied to the sensing sites within the partially-encapsulated sensing chip housing. Thus, all the alignment scanning may occur in one or more pass, and then the controller may send the head back to where it "remembers" the optimized position (peak) to begin reading sample.

As mentioned, the partially-encapsulated sensing chip is typically clamped tightly in the reader, so that a user cannot pull the partially-encapsulated sensing chip (e.g., housing) out until the reader releases it. The partially-encapsulated sensing chip holder may also prevent vibration.

In some variations, the reader beings with the alignment by reading from a "dry" chip in the partially-encapsulated sensing chip. The sample (solution) may be drawn onto (or in some variations across) the chip when reading is to be performed. For example, the sample solution may be either pumped or drawn by capillary force to pull it across the sensing surface of the chip while reading.

Any of the device described herein typically operate by taking measurements either continuously or discretely over time, so as to monitor the binding kinetics of the analyte at the surface of the sensing sites on the chip. From the binding kinetics, a concentration of the analyte may be determined. For example, optical signals measured from the collection waveguides will change over time as more analyte binds/releases from the sensing surface. As the sample solution sits on the sensing sites longer, the binding kinetics may be determined as corresponding to the optical signal (e.g., from a florescent motif on or bound to the analyte). As more analyte is captured on the surface, the optical signal will typically increase until equilibrium. The systems described herein may measure the rate of binding, which may be typical of analyte concentration. Any of the systems described herein may be used with a control/concentration curve based on this kinetics of binding.

For example, in some variations the sensing site(s) on the chip of the partially-encapsulated sensing chip may be configured to include a bound antibody and may act a solid-phase substrate for an ELISA-type binding assay. An antibody specific to a particular analyte may tethered to optical sensing sites of the sensing surface (e.g., at the intersection regions above the collection and/or on the excitation waveguide). The sample solution added to the partially-encapsulated sensing chip (which may be filtered as mentioned above) may be mixed with (e.g., lyophilized) reagents including (for unlabeled analytes) a second antibody that is either directly or indirectly labeled (e.g., via a fluorescently tagged secondary antibody). In general, the added reagents may include any components necessary or helpful for identifying the analyte, e.g., labeling binding partner (antibody, FAB, etc.), non-specific binding blockers, buffer(s), etc. As mentioned above, the positive control may also be included (e.g., printing the binding site for the positive control on one or more of the optical sensing sites) and including labeled positive control in the pre-loaded (e.g., lyophilized) reagents. The observed rate of binding of the positive control may be used to adjust the signals for temperature, age of chip, or the like, and thereby may be used to determine a correction factor for the analyte. For example, in some variations the partially-encapsulated sensing chip (e.g., housing) may be pre-loaded with a dissolvable or lyophilized 'bead' that includes all or some of the reagents. In general the waveguides described herein may be used with multiple wavelengths, and thus multiple excitation and/or collection wavelengths may be used, allowing the same optical sensing sites to be used to detect multiple (or interacting) analytes.

In practice, a partially-encapsulated sensing chip may be aligned and read in less than 10 minutes (e.g., less than 5 minutes, less than 4 min, less than 3 min, less than 2 min, less than 1 min, less than 30 sec). In addition, multiple analytes may be measured at the same time. For example, different optical sensing sites may be coated/prepared with different binding partners for analytes of interest.

In any of these examples, the chip (e.g., the sensing surface of the chip) may also be coated with a protective layer that can be washed/dissolved by the addition of the sample fluid during the assay. For example, a chip may be pre-coated with water-soluble protectant, in addition to the coating of binding partner(s) in the optical sensing site and/or the soluble alignment control marker. In some variation the protective coating is the soluble marker for alignment control. As mentioned, a soluble alignment marker that dissociates from the optical sensing site upon application of the sample may be useful for both pre-aligning and for indicating when sample has contacted the sensing surface; the kinetics of release from the sensing surface may also be used another control for correcting the reading(s) from the chip. In general, the dynamic alignment of the optical head to the chip of the partially-encapsulated sensing chip permits the tolerances in forming and using the chip and housing, potentially reducing the cost and enhancing the operation of the consumable partially-encapsulated sensing chip.

Returning to FIG. 5, proper alignment of the exposed edge(s) with the optical head 521 is important to successfully perform the assay. In some embodiments, the partially-encapsulated sensing chip (e.g. housing) 500 can include brackets, tabs, slots, posts, holes, sockets or other registration features that facilitate the proper insertion, positioning and alignment of the partially-encapsulated sensing chip 500 within the optical reader system 520. In some embodiments, these registration features facilitate a rough alignment between the optical head 521 and the exposed edge(s), which may be within about 200, 100, 150, or 50 µm of proper alignment. Fine alignment can be accomplished, for example, by performing lateral adjustments to the optical head 521 with the actuator 524. In some embodiments, the lateral adjustments can be made in steps of predetermined size, such as about 1, 2, 3, 4, 5, 6, 7, 8, 9, 10, 15, 20, or 25 µm. In other embodiments, the lateral adjustments can be made in a continuous manner. Once proper lateral alignment is achieved, the optical head 521 can be vertically scanned, using for example a piezoelectric actuator or a stepper motor, as described in U.S. Pat. No. 8,675,199, which is herein incorporated by reference in its entirety for all purposes. In some embodiments, by controlling the height of the exposed edge(s) from the base of the partially-encapsulated sensing chip (e.g., housing) to a predetermined value, the exposed edge(s) are in at least rough vertical alignment with the optical head 521 after insertion into the optical reader 520. In some embodiments, if the partially-encapsulated sensing chips come in different predetermined heights, such as three different heights for example, the optical head 521 can be stepped vertically between corresponding predetermined heights to provide rough vertical alignment.

Figure 6:
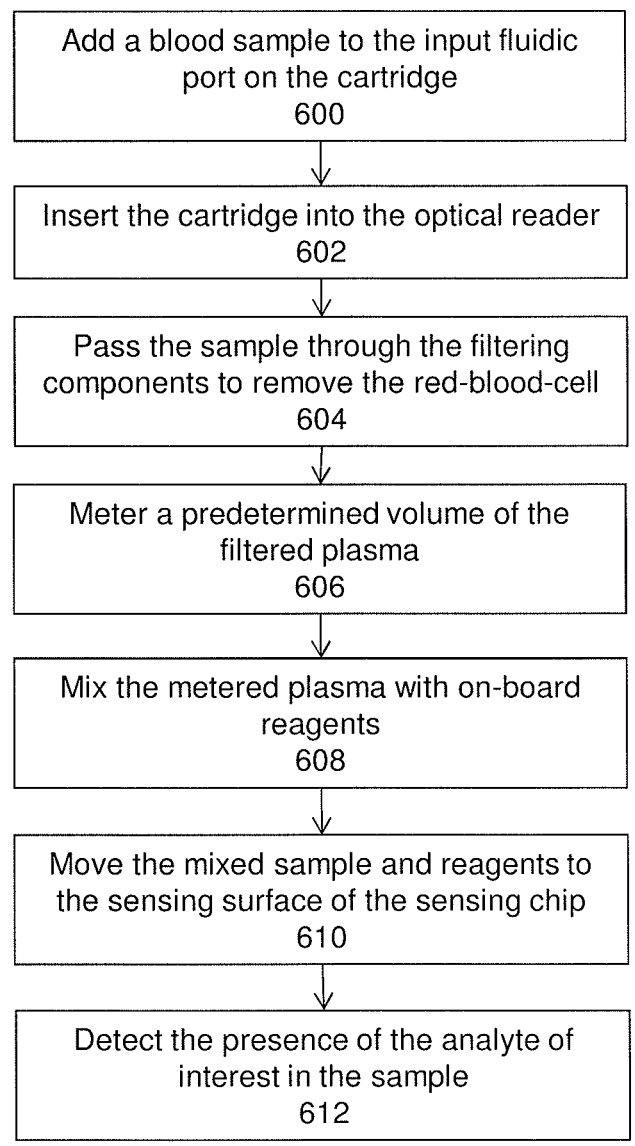
FIG. 6 is a flowchart showing an example of the steps involved in using the partially-encapsulated sensing chip and optical reader.

FIG. 6 illustrates a flow chart showing an embodiment of the steps involved in using the partially-encapsulated sensing chip and optical reader to measure the level of an analyte in a sample. First, in step 600, a blood sample can be added to the input fluidic port on the partially-encapsulated sensing chip (e.g., housing). Then, in step 602, the partially-encapsulated sensing chip can be inserted into the optical reader. In step 604, the sample is passed through the filtering components to remove the red blood cells from the blood sample, leaving filtered plasma. In step 606, a predetermined volume of the filtered plasma can be metered out, and in step 608 the metered plasma can be mixed with the on-board reagents. In step 610, the mixture of the sample and reagents can be moved to the sensing surface of the sensing chip. In step 612, the presence or level of the analyte of interest in the sample is detected. In some embodiments, the ordering of the steps can be altered. For example, in some embodiments, the sample can be passed through the filtering component before the partially-encapsulated sensing chip is inserted into the optical reader. In some embodiments, the filtered plasma can be simultaneously metered and mixed with the on-board reagents.

Figure 7A:
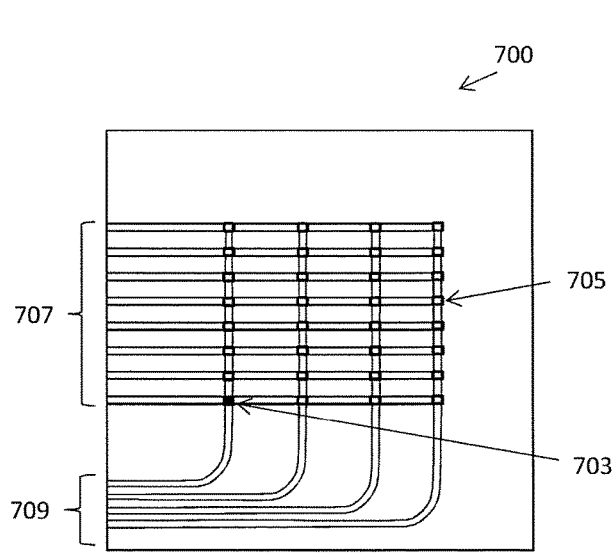
FIG. 7A is a schematic illustration of an example of a sensing chip including collection and excitation waveguides.
Figure 7B:
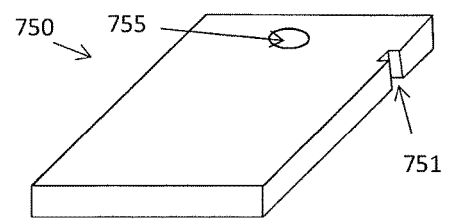
FIGS. 7B and 7C schematically illustrate right and left top perspective views, respectively, of a partially-encapsulated sensing chip including a sensing chip such as the one shown in FIG. 7A.
Figure 7C:
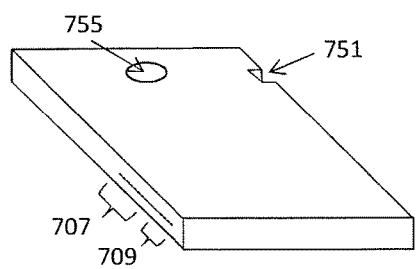
Figure 7D:
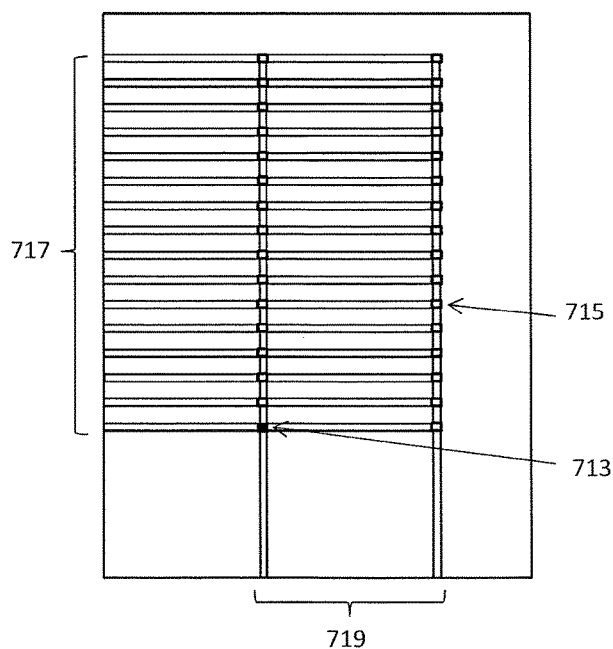
FIG. 7D is a schematic illustration of another example of a sensing chip including collection and excitation waveguides, and FIGS. 7E and 7F schematically illustrate right and left top perspective views, respectively, of a partially-encapsulated sensing chip including a sensing chip such as the one shown in FIG. 7D.

FIGS. 7A and 7D illustrate example of sensing chips that may be used with the apparatuses (systems and devices) described above. For example, in FIG. 7A, the chip includes a plurality of excitation waveguides 709 (showing two excitation waveguides) and a plurality of collection waveguides 707 that cross at optical collection sites 705, which forms part of the upper surface (sensing surface) of the chip. For example, the collection waveguide may be about 50 micronside and about 115 nm deep, and may run directly beneath and adjacent to the excitation waveguide. The side of the excitation waveguide opposite the collection waveguide may from the optical sensing site of the sensing surface onto which the antigen-binding partner may be coupled. A cladding or coating may separate the collection waveguide, excitation waveguide; a cladding or coating may separate the excitation waveguide and the optical sensing surface.

In FIG. 7A, the chip 700 is arranged so that the waveguides all extend to a single edge (side), and the inside of the waveguide are exposed at this side (edge). A 4×8 array of sensing sites is formed by FIG. 7A (with 4 excitation waveguides and eight collection waveguide forming 32 sensing sites). In FIG. 7A one of the sensing sites on the sensing surface is configured as an alignment emitting control 703, and is coated with a marker that emits during alignment (applying excitation to the fourth excitation waveguide and detecting a signal from the first collection waveguide). The marker may be soluble in the sample solution, as discussed above, allowing detection of the addition of sample and/or calibration by tracking the dissociation from the sensing surface as mentioned.

FIGS. 7B and 7C illustrate side perspective views of a partially-encapsulated sensing chip including the chip of FIG. 7A. In this example, the partially-encapsulated sensing chip is housed so that the edge of the chip is exposed, exposing the access into the collection 707 and excitation 709 waveguides on the same side/edge of the housing of the partially-encapsulated sensing chip. The partially-encapsulated sensing chip may include any of the features mentioned above, including an alignment/locking feature on the housing 751, and a fluid access port 755 and one or more venting ports (not shown), valve access regions (not shown) and/or pumping ports (not shown).

Figure 7E:
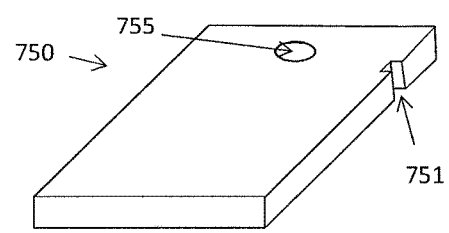
Figure 7F:
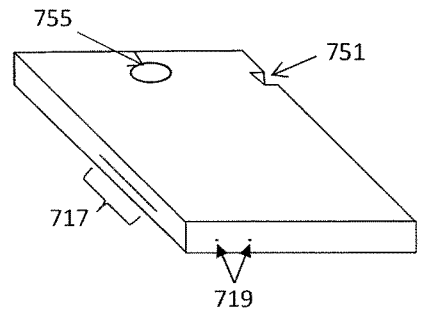

Similarly, FIG. 7D shows another variation of a sensing chip (also not to scale). In this example the chip includes 2 excitation waveguides 719 and 16 collection waveguides 717. As in FIG. 7A, the chip may be small (e.g., less than 3 mm×3 mm). In this example, collection waveguides 719 terminate at the very edge of the chip on a different edge than the collection waveguides 717. Both the collection and excitation waveguide may be accessed from the edge of the chip, and the chip may be held in a housing so that these edges are fully exposed (without any intervening surface between the waveguide and the air, allowing optical coupling through just the air gram from the optical reading head of the reader as described above. FIGS. 7E and 7F illustrate schematically a partially-encapsulated sensing chip including the chip of FIG. 7D. The chip may be positioned in the corner of the housing, and two edges of the chip exposed through the sidewall of the housing, as shown, providing the direct access to the edge of the chip for applying/sensing light efficiently to/from the collection waveguides 717 and the excitation waveguides 719. As in FIGS. 7B and 7C, the partially-encapsulated sensing chip may include any of the features mentioned above, including an alignment/locking feature on the housing 751, and a fluid access ort 755 and one or more venting ports (not shown), valve access regions (not shown) and/or pumping ports (not shown).

In any of the variations described above, the partially-encapsulated sensing chip can be single use and disposable, or alternatively, it could be re-usable or multiple-use.

In some embodiments, the waste reservoir can include or be filled with an absorbent or wicking material to help draw fluid through the partially-encapsulated sensing chip (e.g., housing) using capillary action. The absorbent or wicking material can be hydrophilic.

In some embodiments, the optical reader is powered by an on-board battery. In other embodiments, the optical reader is powered through a conventional power cable. In other embodiments, the optical reader can have a USB connection that can power the optical reader.

In some embodiments, the optical reader can have a USB connection for transferring data to and/or from a computer. In some embodiments, the computer can also be used to control the optical reader and to update software and/or firmware on the optical reader.

In some embodiments, the optical reader may have a wireless communications feature, such as Bluetooth or Wi-Fi, that allows data and/or instructions to be transmitted between the optical reader and another computing device, such as a computer, laptop, notebook, tablet, and smartphone.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for detecting a level of an analyte in a sample; the device comprising:
    a housing;
    a fluidic input port on the housing for receiving the sample;
    a flow channel within the housing in fluid communication with the fluidic input port;
    a sensing chip within the housing, the sensing chip comprising
    a sensing surface in fluid communication with the flow channel,
    an excitation waveguide extending through the sensing chip and exposed at a first side region of the chip,
    a collection waveguide extending through the sensing chip and exposed at a second side region of the chip, wherein the excitation waveguide and the collection waveguide cross and are optically coupled at an optical sensing site on the sensing surface,
    wherein the first side region is exposed at a first outer surface region of the housing for optically coupling directly with the excitation waveguide, and wherein the second side region is exposed at a second outer surface region of the housing for optical coupling directly with the collection waveguide; and
    a waste reservoir within the housing in fluid communication with the flow channel for receiving the sample from the flow channel.

2. The device of claim 1, wherein the sensing chip further comprises an alignment optical sensing site formed at one or more of the optical sensing sites comprising a florescent marker on the optical sensing site.

3. The device of claim 2, wherein the florescent marker on the optical sensing site is water soluble.

4. The device of claim 1, wherein the sensing surface faces away from the input fluidic port and towards the waste reservoir.

5. The device of claim 1, wherein the first side region and the second side region are adjacent to each other.

6. The device of claim 1, wherein the first side region is a first edge region.

7. The device of claim 1, wherein the second side region is a second edge region.

8. The device of claim 1, wherein the first and second outer surface regions form a single optical coupling region on an outer surface of the housing.

9. The device of claim 1, wherein the first outer surface region and the second outer surface region are on the same outer surface of the housing.

10. The device of claim 1, wherein the first outer surface region and the second outer surface region are on different outer surfaces of the housing.

11. The device of claim 1, further comprising a filter upstream of the flow channel for filtering debris and/or red blood cells from the sample before the sensing surface.

12. The device of claim 1, further comprising a chamber between the input fluidic port and the flow channel that comprises one or more reagent storage compartments.

13. The device of claim 1, further comprising a metering and mixing compartment, wherein the metering and mixing compartment has a predetermined volume.

14. The device of claim 1, further comprising a metering and mixing compartment having a predetermined volume, wherein the metering and mixing compartment comprises mixing beads.

15. The device of claim 1, further comprising a metering and mixing compartment having a predetermined volume, wherein the metering and mixing compartment comprises baffles.

16. The device of claim 1, further comprising an elastomer in areas adjacent to the flow channel which can be distended using an external actuator for closing the flow channel.

17. The device of claim 16, further comprising an opening in the housing that provides access to the elastomer for the external actuator, wherein the opening allows the external actuator to access the elastomer for distending the elastomer and closing the flow channel.

18. The device of claim 1, further comprising one or more openings in areas adjacent to the flow channel in the housing which can be in gaseous communication with an external pump and or an external valve for generating negative or positive pressure in the flow channel for pulling or pushing the sample.

19. The device of claim 1, further comprising a capillary channel configured to pull in the sample from the fluidic input port to the flow channel using capillary force.

20. The device of claim 19, wherein the capillary channel has a predetermined volume configured to precisely meter a predetermined volume of the sample.

21. The device of claim 1, wherein the excitation waveguide and the collection waveguide are evanescently coupled at the optical sensing site.

\* \* \* \* \*